US008323885B2

(12) United States Patent
Gecz et al.

(10) Patent No.: US 8,323,885 B2
(45) Date of Patent: Dec. 4, 2012

(54) HOMEOBOX GENE

(75) Inventors: Jozef Gecz, Burnside (AU); Petter Stromme, Oslo (NO)

(73) Assignee: Central Adelaide Local Health Network Incorporated, Adelaide (AU)

( * ) Notice: Subject to any disclaimer, the term of this patent is extended or adjusted under 35 U.S.C. 154(b) by 2132 days.

(21) Appl. No.: 10/496,538

(22) PCT Filed: Nov. 26, 2002

(86) PCT No.: PCT/AU02/01599
§ 371 (c)(1),
(2), (4) Date: Jan. 11, 2005

(87) PCT Pub. No.: WO03/045989
PCT Pub. Date: Jun. 5, 2003

(65) Prior Publication Data
US 2005/0118592 A1 Jun. 2, 2005

(30) Foreign Application Priority Data
Nov. 26, 2001 (AU) .................................. PR9095

(51) Int. Cl.
*C12P 19/34* (2006.01)
*C12Q 1/68* (2006.01)
(52) U.S. Cl. ........................... 435/6.1; 436/63; 435/6.11
(58) Field of Classification Search ........................ None
See application file for complete search history.

(56) References Cited

U.S. PATENT DOCUMENTS
6,197,500 B1  3/2001 Sutherland et al.

FOREIGN PATENT DOCUMENTS
WO    WO 03/045989    6/2003

OTHER PUBLICATIONS

Dipole (2000 ASHG Annual Meeting, 200, p. No. 890, pp. 1).*
GenBank accession AY038071.1 (AY038071.1, gi 15315599, Aug. 27, 2001, pp. 1, available at ncbi.clm.nih.gov).*
Kristensen et al. (Biotechniques, 2001, 30: 318-320, 322, 324, 326, 328-330, 332).*
Gronskov (Eur. J. Human Genetics, 2004, vol. 12, pp. 701-715).*
Gecz (Current Opinion in Genetics and Developments, 2006, vol. 16, pp. 308-316).*
Erichsen et al. (Br J. Cancer, 2004, vol. 90, pp. 747-751).*
Hirshhorn et al. (Genetics in Medicine, 2002, 4(2): 45-61).*
Banerjee-Basu, S. and A.D. Baxevanis, "Molecular Evolution of the Homeodomain Family of Transcription Factors," *Nucleic Acids Research*, 29:3258-3269 (2001).
Bayer, E.A. and M. Wilchek, "Protein Biotinylation," *General Methodology*, 184:138-160 (1990).
Berkovic, S.F. and I.E. Scheffer, "Genetics of the Epilepsies," *Epilepsia*, 42:16-23 (2001).

Brais, B., et al., "Short GCG Expansions in the *PABP2* Gene Cause Occulopharyngeal Muscular Dystrophy," *Nature Genetics*, 18:164-167 (1998).
Brown, S.A., et al., "Holoprosencephaly Due to Mutations in *ZIC2*, a Homologue of *Drosophilia Odd-Paired*," *Nature Genetics*, 20:180-183 (1998).
Brown, L.Y.., et al., "Holoprosencephaly Due to Mutations in *ZIC2*: Alanine Tract Expansion Mutations May be Caused by Parental Somatic Recombination," *Hum. Mol. Genet.*, 10:791-796 (2001).
Brüggemann, M. et al., "Designer Mice: The Production of Human Antibody Repertoires in Transgenic Animals," *Year in Immuno.*, 7:33-40 (1993).
Calado, A., et al., "Nuclear Inclusions in Oculopharyngeal Muscular Dystrophy Consist of Poly(A) Binding Protein 2 Aggregates Which Sequester Poly(A) RNA," *Human Molecular Genetics*, 15:2321-2328 (2000).
Chelly, J. and J.L. Mandel, et al., "Monogenic Causes of X-Linked Mental Retardation," *Nature Reviews*, 2:669-680 (2001).
Claes, S., et al., "The X-Linked Infantile Spasms Syndrome (MIM 308350) Maps to Xp11.4-Xpter in Two Pedigrees," *Ann. Neurol.* 42:360-364 (1997).
Crisponi, L., et al., "The Putative Forkhead Transcription Factor *FOXL2* is Mutated in Blepharophimosis/Ptosis/Epicanthus Inversus Syndrome," *Nature Genetics*, 27:159-166 (2001).
David, G. "Protein Iodination With Solid State Lactoperoxidase," *Biochemistry*, 13(5):1014-1021 (1974).
Feinberg, A. and Leahy, W., "Infantile Spasms: Case Report of Sex-Linked Inheritance," *Dev. Med. Child. Neurol.*, 19(4):524-526 (1977).
Fodde, R., "Losekoot M.Mutation Detection by Denaturing Gradient Gel Electrophoresis (DGGE)," *Hum. Mutat.*, 3(2):83-94 (1994).
Frohman, M.A., et al., "Rapid Production of Full-Length cDNAs from Rare Transcripts: Amplification Using a Single Gene-Specific Oligonucleotide Primer," *Proc. Natl. Acad. Sci.*, 85:8998-9002 (1988).
Galliot, B. and D. Miller, "Origin of Anterior Patterning How Old is Our Head?", *TIG* 16:1-4 (2000).
Galliot, B., et al., "Evolution of Homeobox Genes: $Q_{50}$ Paired-Like Genes Founded the Paired Class," *Dev. Genes Evol.*, 209:186-197 (1999).
Gaspar, C., et al., "CAG Trace of MJD-1 May be Prone to Frameshifts Causing Polyalanine Accumulation," *Human Molecular Genetics*, 13: 1957-1966 (2000).
Goodman, F.R., et al., "Nove H XA13 Mutations and the Phenotypic Spectrum of Hand-Foot-Genita Syndrome," *Am. J. Hum. Genet.* 67:197-202 (2000).
Guesella, J.F. and M.E. MacDonald, "Molecular Genetics: Unmasking Polyglutatmine Triggers in Neurodegenerative Disease," *Nature Reviews*, 1:109-116 (2000).
Hill, M.E., et al., "Oculopharyngeal Muscular Dystrophy Phenotypic and Genotypic Studies in a UK Population," *Brain*, 124:522-526 (2001).
Hoogenboom, H. and Winter, G. et al., "By-Passing Immunisation. Human Antibodies From Synthetic Repertoires of Germline VH Gene Segments Rearranged in Vitro, *J. Mol. Biol.*, 227(2):381-8 (1992).

(Continued)

*Primary Examiner* — Sarae Bausch
(74) *Attorney, Agent, or Firm* — Hamilton, Brook, Smith & Reynolds, P.C.

(57) ABSTRACT

An isolated nucleic acid molecule comprising the nucleotide sequence set forth in SEQ ID NO: 1.

11 Claims, 4 Drawing Sheets

OTHER PUBLICATIONS

Jakobovits, A. et al., "Analysis of Homozygous Mutant Chimeric Mice: Deletion of the Immunoglobulin Heavy-Chain Joining Region Blocks B-Cell Development and Antibody Production," *Proc. Natl. Acad. Sci.*, 90:2551-2555 (1993).

Jakobovits, A. et al., "Germ-Line Transmission and Expression of a Human-Derived Yeast Artificial Chromosome," *Nature*, 362(6417):255-258 (1993).

Jones, P. et al., "Replacing the Complementarity-Determining Regions in a Human Antibody With Those From a Mouse," *Nature*, 321(6069):522-525 (1986).

Kitamura, K. et al., "Mutation of ARX Causes Abnormal Development of Forebrain and Testes in Mice and X-Linked Lissencephaly With Abnormal Genitalia in Humans," *Nature Genetics*, 32:359-369 (2002).

Kohler, G. and Milstein, C., "Continuous Cultures of Fused Cells Secreting Antibody of Predefined Specificity," *Nature*, 256(5517):495-497 (1975).

Kozbor, D. et al., "A Human Hybrid Myeloma for Production of Human Monoclonal Antibodies," *J. Immunol.*, 133(6):3001-3005 (1984).

Kristensen V. et al., "High-Throughput Methods for Detection of Genetic Variation," *Biotechniques*, 30(2):318-22, 324, 326 passim (2001).

Leushner, J., "MALDI TOF mass spectrometry: an emerging platform for genomics and diagnostics," *Expert. Rev. Mol. Diagn.*, 1(1):11-8 (2001).

Lewis, B.H. et al., "Confirmation of Linkage in X-Linked Infantile Spasms (West Syndrome) and Refinement of the Disease Locus to Xp21.3-Xp22.1," *Clin. Genet.*, 55:173-181 (1999).

Marks, J. et al., "By-Passing Immunization. Human Antibodies From V-Gene Libraries Displayed on Phage," *J. Mol. Biol.*, 222(3):581-97 (1991).

McKenzie, S.E., et al., "Parallel Molecular Genetic Analysis," *Eur. Jour. Hum. Genet.*, 6:4170429 (1998).

Meijlink, F., et al., "Vertebrate Aristaless-Related Genes," *Int. J. Dev. Biol.* 43:651-663 (1999).

Miura, H., et al., "Expression of a Novel Aristaless Related Homeobox Gene 'Arx' in the Vertebrate Telecephalon, Diencephalon and Floor Plate," *Mechanisms of Development*, 65:99-109 (1997).

Morrison, S.L., et al., "Chimeric Human Antibody Molecules: Mouse Antigen-Binding Domains with Human Constant Region Domains," *Proc. Natl. Acad. Sci.*, 81:6851-6855 (1984).

Mullis, K. and Faloona, F., "Specific Synthesis of DNA In Vitro Via a Polymerase-Catalyzed Chain Reaction," *Methods Enzymol.*, 155:335-350 (1987).

Mundlos, S., et al., "Mutations Involving the Transcription Factor CBFA1 Cause Cleidocranial Dysplasia," *Cell*, 89:773-779 (1997).

Muragaki, Y. et al., "Altered Growth and Branching Patterns in Synpolydactyly Caused by Mutations in HOXID13," *Science*, 272(5261):548-551 (1996).

Nataraj, A. et al., "Single-Strand Conformation Polymorphism and Heteroduplex Anaylsis for Gel-Based Mutation Detection," *Electrophoresis*, 20(6):1177-85 (1999).

Ohira, R., et al., "Human ARX Gene: Genomic Characterization and Expression," *Molecular Genetics and Metabolism*, 77:179-188 (2002).

Pain, D. and A. Surolia, "Preparation of Protein A-Peroxidase Monoconjugate Using a Heterobifunctional Reagent, and Its Use in Enzyme Immonoassays," *Jour. Immun. Met.* 40:219-230 (1981).

Partington, M.W., et al., "X-Linked Mental Retardation with Dystonic Movements of the Hands," *Am. Jour. Med. Genet.* 30:251-262 (1988).

Rankin, J., et al., "Intracellular Green Fluorescent Protein-Polyalanine Aggregates are Associated with Cell Death," *Biochem. J.*, 348:15-19 (2000).

Richards, R.I., "Dynamic Mutations: A Decade of Unstable Expanded Repeats in Human Genetic Disease," *Human Molecular Genetics*, 10:2187-2194 (2001).

Riechmann, L. et al., "Reshaping Human Antibodies for Therapy," *Nature*, 332(6162):323-327 (1988).

Saiki, R. et al., "Primer-Directed Enzymatic Amplification of DNA With a Thermostable DNA Polymerase," *Science*, 239:487-491 (1988).

Stevenson, R., "Splitting and Lumping in the Nosology of XLMR," *Am. J. Med. Genet.*, 97(3):174-182 (2000).

Stromme, P., et al., "X Linked Mental Retardation and Infantile Spasms in a Family: New Clinical Data and Linkage to Xp11.4-Xp22.11," *J. Med. Genet.* 36:374-378 (1999).

Stromme, P., et al., "Mutations in the Human Ortholog of Aristaless Cause X-Linked Mental Retardation and Epilpsey," *Nature Genetics*, 30:441-445 (2002).

Sugawara, T., et al., "A Missense Mutation of the Na+ Channel $\alpha_{II}$ Subunit Gene $Na_v1.2$ in a Patient with Febrile and aFebrile Seizures Causes Channel Dysfunction," *Proc. Natl. Acad. Sci.*, 98: 6384-6389 (2001).

Triglia, T., et al., "A Procedure for in vitro Amplification of DNA Segments that Lie Outside the Boundaries of Known Sequences," *Nuc. Acids Res.*, 16: 8186 (1988).

Verhoeyen, M. et al., "Reshaping Human Antibodies: Grafting an Antilysozyme Activity," *Science*, 239(4847):1534-1536 (1988).

Vigevano, F. et al., "The idiopathic form of West syndrome," *Epilepsia*, 34(4):743-746 (1993).

Wilson, D.S., et al., "Conservations and Diversifications in Homeodomain=DNA Interactions: A Comparative Genetic Analysis," *Proc. Natl. Acad. Sci.*, 93:6886-6891 (1996).

Wong, M. and Trevathan, E., "Infantile spasms," *Pediatr. Neurol.*, 24(2):89-98 (2001).

Gen Pept accession No. AAK93901; Ohira, R.N., et al. submitted Jun. 5, 2001.

Gen Pept accession No. BAA85852; Ohsaki, K., et al. submitted Apr. 24, 1999.

Swiss-Prot. accession No. O35085.

Swiss-Prot. accession No. O42115.

Gen Pept accession No. BAA28284.

Gecz, J., et al., "ARX: A Gene for all Seasons," *Curr. Opin. in Genet. & Dev.*, 16:1-9 (2006) (month not available).

\* cited by examiner

FIG 1b a b

SEQUENCE LISTING

<160> NUMBER OF SEQ ID NOS: 48

<210> SEQ ID NO 1
<211> LENGTH: 1689
<212> TYPE: DNA
<213> ORGANISM: Homo sapiens

<400> SEQUENCE: 1

```
atgagcaatc agtaccagga ggagggctgc tccgagaggc ccgagtgcaa aagtaaatct      60
ccaactttgc tctcctccta ctgcatcgac agcatcctgg gccggaggag cccgtgcaaa     120
atgcggttgc tgggagccgc gcagagcttg cctgctccgc tgaccagccg cgccgacccg     180
gaaaaggccg tgcaaggctc ccctaagagc agcagcgccc cgttcgaggc cgagctgcac     240
ctgccgccca agctgcggcg cctgtacggc ccggcgggg gccgcctcct tcagggtgcg     300
gcagcggcgg cggcggcggc ggcggcggcg gcggcagcgg ccgccacggc cacggcgggt     360
ccacgcgggg aggcccctcc gccgccaccg ccaaccgcgc ggcccgggga acggccggac     420
ggcgcagggg ccgccgcggc agccgcggcc gggccgccgc cggcctggga cacgctcaag     480
atcagccagg cgccgcaggt gagcatcagc cgcagcaagt cgtaccgcga gaacgggcg     540
```

```
cccttcgtgc cgccgccgcc cgcgctggac gagctgggcg gcccgggggg cgtcacgcac     600
ccggaggagc gcctcggcgt ggccggcggc ccgggcagcg ccccggctgc gggtggtggc     660
accggcaccg aggacgacga ggaggagctg ctggaggacg aagaagatga ggacgaggaa     720
gaggaactgc tggaggacga cgaggaggag ctgctggagg acgacgcccg cgcgctgctc     780
aaggagcccc ggcgctgtcc tgtggccgcc actggcgccg tggccgcagc agctgccgct     840
gcagtggcca cagagggcgg ggagctgtca cccaaggagg agctgctgct gcacccggaa     900
gacgctgagg caaggacggc cgaggacagc gtgtgcctct ctgcgggcag cgactcggag     960
gaggggctgc tgaaacgcaa acagaggcgc taccgcacca cgttcaccag ctaccagctg    1020
gaggaactgg agcgggcctt ccagaagacg cactacccgg acgtcttcac cagggaggaa    1080
ctggccatga ggctggactt gaccgaggcc cgagtccagg tctggttcca gaaccgtcgg    1140
gccaagtggc gcaagcggga aaggcaggcg cgcagaccca ccccccctgg gctgcccttc    1200
ccggggccgc tctccgccac ccacccgctc agccccctacc tggacgccag ccccttccct    1260
ccgcaccacc cggcgctcga ctccgcttgg actgccgctg ccgccgccgc cgccgccgcc    1320
ttcccgagcc tacctccgcc tccgggctcg gccagcctgc cgcccagcgg ggcgccgctg    1380
ggcctgagca ctttcctcgg agcggcagtg ttccgacacc cagctttcat cagcccggca    1440
ttcggcaggc tcttttccac aatggccccc ctgaccagcg cgtcgaccgc ggccgcgctc    1500
ctgagacagc ccacacccgc cgtggagggc gcagtggcat cgggcgccct ggccgacccg    1560
gccacggcgg ccgcagacag acgcgcctct agcatagccg cgctgaggct caaggccaag    1620
gagcacgcgg cgcagctcac gcagctcaac atcctgccgg gcaccagcac gggcaaggag    1680
gtgtgctaa                                                            1689
```

<210> SEQ ID NO 2
<211> LENGTH: 562
<212> TYPE: PRT
<213> ORGANISM: Homo sapiens

<400> SEQUENCE: 2

Met Ser Asn Gln Tyr Gln Glu Glu Gly Cys Ser Glu Arg Pro Glu Cys
1               5                   10                  15

Lys Ser Lys Ser Pro Thr Leu Leu Ser Ser Tyr Cys Ile Asp Ser Ile
            20                  25                  30

Leu Gly Arg Arg Ser Pro Cys Lys Met Arg Leu Leu Gly Ala Ala Gln
        35                  40                  45

Ser Leu Pro Ala Pro Leu Thr Ser Arg Ala Asp Pro Glu Lys Ala Val
    50                  55                  60

Gln Gly Ser Pro Lys Ser Ser Ala Pro Phe Glu Ala Glu Leu His
65                  70                  75                  80

Leu Pro Pro Lys Leu Arg Arg Leu Tyr Gly Pro Gly Gly Gly Arg Leu
                85                  90                  95

Leu Gln Gly Ala Ala Ala Ala Ala Ala Ala Ala Ala Ala Ala Ala Ala
            100                 105                 110

Ala Ala Ala Thr Ala Thr Ala Gly Pro Arg Gly Glu Ala Pro Pro
        115                 120                 125

Pro Pro Pro Thr Ala Arg Pro Gly Glu Arg Pro Asp Gly Ala Gly Ala
    130                 135                 140

Ala Ala Ala Ala Ala Ala Ala Ala Ala Ala Trp Asp Thr Leu Lys
145                 150                 155                 160

Ile Ser Gln Ala Pro Gln Val Ser Ile Ser Arg Ser Lys Ser Tyr Arg

```
                        165                 170                 175
Glu Asn Gly Ala Pro Phe Val Pro Pro Pro Ala Leu Asp Glu Leu
                180                 185                 190

Gly Gly Pro Gly Gly Val Thr His Pro Glu Glu Arg Leu Gly Val Ala
            195                 200                 205

Gly Gly Pro Gly Ser Ala Pro Ala Ala Gly Gly Thr Gly Thr Glu
            210                 215                 220

Asp Asp Glu Glu Glu Leu Leu Glu Asp Glu Glu Asp Glu Asp Glu Glu
225                 230                 235                 240

Glu Glu Leu Leu Glu Asp Asp Glu Glu Glu Leu Leu Glu Asp Asp Ala
                245                 250                 255

Arg Ala Leu Leu Lys Glu Pro Arg Arg Cys Pro Val Ala Ala Thr Gly
                260                 265                 270

Ala Val Ala Ala Ala Ala Ala Ala Val Ala Thr Glu Gly Gly Glu
            275                 280                 285

Leu Ser Pro Lys Glu Glu Leu Leu Leu His Pro Glu Asp Ala Glu Gly
            290                 295                 300

Lys Asp Gly Glu Asp Ser Val Cys Leu Ser Ala Gly Ser Asp Ser Glu
305                 310                 315                 320

Glu Gly Leu Leu Lys Arg Lys Gln Arg Arg Tyr Arg Thr Thr Phe Thr
                325                 330                 335

Ser Tyr Gln Leu Glu Glu Leu Glu Arg Ala Phe Gln Lys Thr His Tyr
                340                 345                 350

Pro Asp Val Phe Thr Arg Glu Glu Leu Ala Met Arg Leu Asp Leu Thr
                355                 360                 365

Glu Ala Arg Val Gln Val Trp Phe Gln Asn Arg Arg Ala Lys Trp Arg
370                 375                 380

Lys Arg Glu Lys Ala Gly Ala Gln Thr His Pro Pro Gly Leu Pro Phe
385                 390                 395                 400

Pro Gly Pro Leu Ser Ala Thr His Pro Leu Ser Pro Tyr Leu Asp Ala
                405                 410                 415

Ser Pro Phe Pro Pro His His Pro Ala Leu Asp Ser Ala Trp Thr Ala
                420                 425                 430

Ala Ala Ala Ala Ala Ala Ala Phe Pro Ser Leu Pro Pro Pro
            435                 440                 445

Gly Ser Ala Ser Leu Pro Pro Ser Gly Ala Pro Leu Gly Leu Ser Thr
            450                 455                 460

Phe Leu Gly Ala Ala Val Phe Arg His Pro Ala Phe Ile Ser Pro Ala
465                 470                 475                 480

Phe Gly Arg Leu Phe Ser Thr Met Ala Pro Leu Thr Ser Ala Ser Thr
                485                 490                 495

Ala Ala Ala Leu Leu Arg Gln Pro Thr Pro Ala Val Glu Gly Ala Val
            500                 505                 510

Ala Ser Gly Ala Leu Ala Asp Pro Ala Thr Ala Ala Asp Arg Arg
            515                 520                 525

Ala Ser Ser Ile Ala Ala Leu Arg Leu Lys Ala Lys Glu His Ala Ala
            530                 535                 540

Gln Leu Thr Gln Leu Asn Ile Leu Pro Gly Thr Ser Thr Gly Lys Glu
545                 550                 555                 560

Val Cys

<210> SEQ ID NO 3
<211> LENGTH: 3151
<212> TYPE: DNA
```

<213> ORGANISM: Homo sapiens

<400> SEQUENCE: 3

```
aggaagagga tagcggactt agaaaattgg taacttaaaa aaagaaagaa agaaaaggaa      60
aattggctct ggtgcgtgcc cgctgccccc acccccgcct gccctctgg aatccagtcc      120
gggctttgcg ccgcgcccac aggccgacgc agcccggcct ctggcgagag ccaatcagag     180
ggcgcctctc agcacgtgga ggagagagac tccagagctc agcgcccgct gctcactaca     240
cttgttaccg cttgtcctga gcgcggagag ggcgagctcg ggccgcgggc agggcgggag     300
ccggcagccg gcaaccaagg gaggcagaaa ggcacaaaga tcgcaataat atccgttata     360
acccgctatc taaccccacc cccaacacac acccatccat cccaccctcc gggagaggca     420
gccggcgatc cgctctctgc gccctgggaa aaagccccag ccatgagcaa tcagtaccag     480
gaggagggct gctccgagag gcccgagtgc aaaagtaaat ctccaacttt gctctcctcc     540
tactgcatcg acagcatcct gggccggagg agcccgtgca aaatgcggtt gctgggagcc     600
gcgcagagct tgcctgctcc gctgaccagc cgcgccgacc cggaaaaggc cgtgcaaggc     660
tcccctaaga gcagcagcgc cccgttcgag gccgagctgc acctgccgcc caagctgcgg     720
cgcctgtacg gcccgggcgg gggccgcctc cttcagggtg cggcagcggc ggcggcggcg     780
gcggcggcgg cggcggcagc ggccgccacg gccacggcgg gtccacgcgg ggaggcccct     840
ccgccgccac cgccaaccgc gcggcccggg gaacggccgg acggcgcagg ggccgccgcg     900
gcagccgcgg ccgcggccgc cgcggcctgg gacacgctca agatcagcca ggcgccgcag     960
gtgagcatca gccgcagcaa gtcgtaccgc gagaacgggg cgcccttcgt gccgccgccg     1020
cccgcgctgg acgagctggg cggccccggg ggcgtcacgc acccggagga gcgcctcggc     1080
gtggccggcg gcccgggcag cgcccccggct gcgggtggtg gcaccggcac cgaggacgac     1140
gaggaggagc tgctggagga cgaagaagat gaggacgagg aagaggaact gctggaggac     1200
gacgaggagg agctgctgga ggacgacgcc cgcgcgctgc tcaaggagcc ccggcgctgt     1260
cctgtggccg ccactggcgc cgtggccgca gcagctgccg ctgcagtggc cacagagggc     1320
ggggagctgt cacccaagga ggagctgctg ctgcacccgg aagacgctga gggcaaggac     1380
ggcgaggaca gcgtgtgcct ctctgcgggc agcgactcgg aggaggggct gctgaaacgc     1440
aaacagaggc gctaccgcac cacgttcacc agctaccagc tggaggaact ggagcgggcc     1500
ttccagaaga cgcactaccc ggacgtcttc accagggagg aactggccat gaggctggac     1560
ttgaccgagc cccgagtcca ggtctggttc cagaaccgtc gggccaagtg cgcaagcgg     1620
gagaaggcag gcgcgcagac ccacccccct gggctgcct tcccgggcc gctctccgcc     1680
acccaccgc tcagccccta cctggacgcc agcccttcc ctccgcacca cccggcgctc     1740
gactccgctt ggactgccgc tgccgccgcc gccgccgccg ccttcccgag cctacctccg     1800
cctccgggct cggccagcct gccgcccagc ggggcgccgc tgggcctgag cactttcctc     1860
ggagcggcag tgttccgaca cccagctttc atcagcccgg cattcggcag gctctttcc     1920
acaatgcccc ccctgaccag cgcgtcgacc gcggccgcgc tcctgagaca gcccacaccc     1980
gccgtggagg gcgcagtggc atcgggcgcc ctggccgacc cggccacggc ggccgcagac     2040
agacgcgcct ctagcatagc cgcgctgagg ctcaaggcca aggagcacgc ggcgcagctc     2100
acgcagctca acatcctgcc gggcaccagc acgggcaagg aggtgtgcta aaggctgccc     2160
tccacacccg cgccccgcgc gcgccccgaa aggtcacctc actcagcacc actcaagacc     2220
aaatggaaac agaggaccag cacactcccg agacggcact gagagagcgc agccgccttc     2280
```

```
acagcagtct ggatgcgggc atggcagccc tcggcgctcc gggacgtggc acctcctcgg    2340
ctggctgtcc acccgcccct gcccctgccc ctgctactgc caacctcgct ccaactccaa    2400
catccactct ctcttgttct tactttcctg aaaatatcgg ggaggttttc tcccccagac    2460
gcctgatatt gaagtaaaaa atttaaaaag cccaacctct tcctcctgac accccactta    2520
gcctttcttt tcttctttct ttcttttctt tttttttta aatagcattt tggcgctcga    2580
agttgatctc cccagcgagg gccccagcgt gaagccaggg cccgggaagc aaatgcgagc    2640
ctgtaagata gctaacagtg cacttaaagg aaagggcgt cttgttcttg ttctcttctt    2700
tatcatacac caaccaaggt ttttatatca aaccaaaggg aaataatact ctgctagaat    2760
atggactgtt gaagtcacca aactgtgatt attgattctg tacataccat tgttattaaa    2820
aaaaaaaaaa aaagaacaga gctttgtata tttgaaatgt tataacgcaa ttgcactcag    2880
cgtggtatgg taaaagtttg tcctcccgta gattcttact gtgttgtaga tacggtaggg    2940
ttcctagaca aatatttatg tactcaagcc ctttatttaa cttattaact gtagaggctt    3000
ccgaaacctt caagataaag gcaatggtac agtacttttg tgtaatgtgt aattgttacc    3060
acttttcctt gctatctagt ggagaagtgt cacgctcaaa ataaaaaaat tatatgttta    3120
acaaaacgaa gtgtgaatgc tccatacagg c                                   3151

<210> SEQ ID NO 4
<211> LENGTH: 1710
<212> TYPE: DNA
<213> ORGANISM: Homo sapiens

<400> SEQUENCE: 4
atgagcaatc agtaccagga ggagggctgc tccgagaggc ccgagtgcaa aagtaaatct      60
ccaactttgc tctcctccta ctgcatcgac agcatcctgg gccggaggag cccgtgcaaa     120
atgcggttgc tgggagccgc gcagagcttg cctgctccgc tgaccagccg cgccgacccg     180
gaaaaggccg tgcaaggctc ccctaagagc agcagcgccc cgttcgaggc cgagctgcac     240
ctgccgccca gctgcggcg cctgtacggc ccgggcgggg gccgcctcct tcagggtgcg     300 gcagcggcg cggcggcggc ggcggcggcg cggcggcggc ggcggcagcg     360
gccgccacgg ccacggcggg tccacgcggg gaggcccctc cgccgccacc gccaaccgcg     420
cggcccgggg aacggccgga cggcgcaggg gccgccgcgg cagccgcggc cgcggccgcc     480
gcggcctggg acacgctcaa gatcagccag gcgccgcagg tgagcatcag ccgcagcaag     540
tcgtaccgcg agaacgggc gcccttcgtg ccgccgccgc ccgcgctgga cgagctgggc     600
ggcccggggg gcgtcacgca cccggaggag cgcctcggcg tggccggcgg cccgggcagc     660
gccccggctg cgggtggtgg caccggcacc gaggacgacg aggaggagct gctggaggac     720
gaagaagatg aggacgagga agaggaactg ctggaggacg acgaggagga gctgctggag     780
gacgacgccc gcgcgctgct caaggagccc ggcgctgtc ctgtggccgc cactggcgcc     840
gtggccgcag cagctgccgc tgcagtggcc acagagggcg gggagctgtc acccaaggag     900
gagctgctgc tgcaccccga agacgctgag ggcaaggacg cgcaggacag cgtgtgcctc     960
tctgcgggca gcgactcgga ggaggggctg ctgaaacgca acagaggcg ctaccgcacc    1020 acgttcacca gctaccagct ggaggaactg gagcggccct tccagaagac gcactacccg    1080
gacgtcttca ccagggagga actggccatg aggctggact tgaccgaggc ccgagtccag    1140
gtctggttcc agaaccgtcg ggccaagtgg cgcaagcggg agaaggcagg cgcgcagacc    1200 caccccccctg ggctgcccct cccggggccg ctctccgcca ccacccgct cagcccctac    1260
```

| | |
|---|---|
| ctggacgcca gcccctteee teegeaccac ceggegcteg actecgcttg gactgccgct | 1320 |
| gecgccgccg ccgccgccgc ctteccgage ctacctccgc cteegggcte ggccagcctg | 1380 |
| ccgcccagcg gggcgccgct gggcctgagc actttcctcg gagcggcagt gttccgacac | 1440 |
| ccagcttttca tcagcccggc attcggcagg ctcttttcca caatggcccc cctgaccagc | 1500 |
| gcgtcgaccg cggccgcgct cctgagacag cccacacccg ccgtggaggg cgcagtggca | 1560 |
| tcgggcgccc tggccgaccc ggccacggcg ccgcagaca gacgcgcctc tagcatagcc | 1620 |
| gcgctgaggc tcaaggccaa ggagcacgcg gcgcagctca cgcagctcaa catcctgccg | 1680 |
| ggcaccagca cgggcaagga ggtgtgctaa | 1710 |

<210> SEQ ID NO 5
<211> LENGTH: 1713
<212> TYPE: DNA
<213> ORGANISM: Homo sapiens

<400> SEQUENCE: 5

| | |
|---|---|
| atgagcaatc agtaccagga ggagggctgc tccgagaggc ccgagtgcaa aagtaaatct | 60 |
| ccaactttgc tctcctccta ctgcatcgac agcatcctgg gccggaggag cccgtgcaaa | 120 |
| atgcggttgc tgggagccgc gcagagcttg cctgctccgc tgaccagccg cgccgacccg | 180 |
| gaaaaggccg tgcaaggctc ccctaagagc agcagcgccc cgttcgaggc cgagctgcac | 240 |
| ctgccgccca gctgcggcg cctgtacggc ccgggcgggg gccgcctcct tcagggtgcg | 300 |
| gcagcggcgg cggcggcggc ggcggcggcg cggcagcgg ccgccacggc cacggcgggt | 360 |
| ccacgcgggg aggcccctcc gccgccaccg ccaaccgcgc ggcccgggga acggccggac | 420 |
| ggcgcagggg ccgccgcggc agccgcggcc gggccgccg cggcagccgc ggccgcggcc | 480 |
| gccgcggcct gggacacgct caagatcagc caggcgccgc aggtgagcat cagccgcagc | 540 |
| aagtcgtacc gcgagaacgg ggcgcccttc gtgccgccgc cgcccgcgct ggacgagctg | 600 |
| ggcggccgg ggggcgtcac gcacccggag gagcgcctcg gcgtggccgg cggcccgggc | 660 |
| agcgccccgg ctgcgggtgg tggcaccggc accgaggacg acgaggagga gctgctggag | 720 |
| gacgaagaag atgaggacga ggaagaggaa ctgctggagg acgacgagga ggagctgctg | 780 |
| gaggacgacg cccgcgcgct gctcaaggag cccggcgct gtcctgtggc cgccactggc | 840 |
| gccgtggccg cagcagctgc cgctgcagtg gccacagagg gcggggagct gtcacccaag | 900 |
| gaggagctgc tgctgcaccc ggaagacgct gagggcaagg acggcgagga cagcgtgtgc | 960 |
| ctctctgcgg gcagcgactc ggaggagggg ctgctgaaaac gcaaacagag gcgctaccgc | 1020 |
| accacgttca ccagctacca gctggaggaa ctggagcggg ccttccagaa gacgcactac | 1080 |
| ccggacgtct tcaccaggga ggaactggcc atgaggctgg acttgaccga ggcccgagtc | 1140 |
| caggtctggt tccagaaccg tcgggccaag tggcgcaagc gggagaaggc aggcgcgcag | 1200 |
| acccacccc ctgggctgcc cttcccgggg ccgctctccg ccaccacccc gctcagcccc | 1260 |
| tacctggacg ccagcccctt ccctccgcac acccggcgc tcgactccgc ttggactgcc | 1320 |
| gctgccgccg ccgccgccgc cgccttcccg agcctacctc cgcctccggg ctcggccagc | 1380 |
| ctgccgccca gcgggcgcc gctgggcctg agcactttcc tcggagcggc agtgttccga | 1440 |
| cacccagctt tcatcagccc ggcattcggc aggctctttt ccacaatggc ccccctgacc | 1500 |
| agcgcgtcga ccgcggccgc gctcctgaga cagcccacac ccgccgtgga gggcgcagtg | 1560 |
| gcatcgggcg ccctggccga cccggccacg gcgccgcag acagacgcgc ctctagcata | 1620 |
| gccgcgctga ggctcaaggc caaggagcac gcggcgcagc tcacgcagct caacatcctg | 1680 |

-continued

| | |
|---|---|
| ccgggcacca gcacgggcaa ggaggtgtgc taa | 1713 |

<210> SEQ ID NO 6
<211> LENGTH: 1448
<212> TYPE: DNA
<213> ORGANISM: Homo sapiens

<400> SEQUENCE: 6

| | |
|---|---|
| atgagcaatc agtaccagga ggagggctgc tccgagaggc ccgagtgcaa aagtaaatct | 60 |
| ccaactttgc tctcctccta ctgcatcgac agcatcctgg gccggaggag cccgtgcaaa | 120 |
| atgcggttgc tgggagccgc gcagagcttg cctgctccgc tgaccagccg cgccgacccg | 180 |
| gaaaaggccg tgcaaggctc ccctaagagc agcagcgccc cgttcgaggc cgagctgcac | 240 |
| ctgccgccca gctgcggcg cctgtacggc ccgggcgggg gccgcctcct tcagggtgcg | 300 |
| gcagcggcgg cggcggcggc ggcggcggcg gcggcagcgg ccgccacggc cacggcgggt | 360 |
| ccacgcgggg aggcccctcc gccgccaccg ccaaccgcgc ggcccgggga acggccggac | 420 |
| ggcgcagggg ccgccgcggc agccgcggcc gcggccgccg cggcctggga cacgctcaag | 480 |
| atcagccagg cgccgcaggt gagcatcagc cgcagcaagt cgtaccgcga gaacggggcg | 540 |
| cccttcgtgc cgccgccgcc cgcgctggac gagctgggcg gccgggggg cgtcacgcac | 600 |
| ccggaggagc gcctcggcgt ggccggcggc ccggcagcg ccccggctgc gggtggtggc | 660 |
| accggcaccg aggacgacga ggaggagctg ctggaggacg aagaagatga ggacgaggaa | 720 |
| gaggaactgc tggaggacga cgaggaggag ctgctggagg acgacgcccg cgcgctgctc | 780 |
| aaggagcccc ggcgctgtcc tgtggccgcc actggcgccg tggccgcagc agctgccgct | 840 |
| gcagtggcca cagagggcgg ggagctgtca cccaaggagg agctgctgct gcacccggaa | 900 |
| gacgctgagg gcaaggacgg cgaggacagc gtgtgcctct ctgcgggcag cgactcggag | 960 |
| gagggggctgc tgaaacgcaa acagaggcgc taccgcacca cgttcaccag ctaccagctg | 1020 |
| gaggaactgg agcgggcctt ccagaagacg cactacccgg acgtcttcac cagggaggaa | 1080 |
| ctggccatga gcctggactt gaccgaggcc cgagtccagg tctggttcca gaaccgtcgg | 1140 |
| gccaagtggc gcaagcggga aaggcaggc gcgcagaccc accccctgg gctgcccttc | 1200 |
| ccggggccgc tctccgccac ccacccgctc agccctacc tggacgccag ccccttccct | 1260 |
| ccgcaccacc cggcgctcga ctccgcttgg actgccgctg ccgccgccgc cgccgccgcc | 1320 |
| ttcccgagcc tacctccgcc tccgggctcg gccagcctgc cgcccagcgg ggcgccgctg | 1380 |
| ggcctgagca ctttcctcgg agcggcagtg ttccgacacc cagctttcat cagcccggca | 1440 |
| ttcggcag | 1448 |

<210> SEQ ID NO 7
<211> LENGTH: 1689
<212> TYPE: DNA
<213> ORGANISM: Homo sapiens

<400> SEQUENCE: 7

| | |
|---|---|
| atgagcaatc agtaccagga ggagggctgc tccgagaggc ccgagtgcaa aagtaaatct | 60 |
| ccaactttgc tctcctccta ctgcatcgac agcatcctgg gccggaggag cccgtgcaaa | 120 |
| atgcggttgc tgggagccgc gcagagcttg cctgctccgc tgaccagccg cgccgacccg | 180 |
| gaaaaggccg tgcaaggctc ccctaagagc agcagcgccc cgttcgaggc cgagctgcac | 240 |
| ctgccgccca gctgcggcg cctgtacggc ccgggcgggg gccgcctcct tcagggtgcg | 300 |
| gcagcggcgg cggcggcggc ggcggcggcg gcggcagcgg ccgccacggc cacggcgggt | 360 |

-continued

```
ccacgcgggg aggcccctcc gccgccaccg ccaaccgcgc ggcccgggga acggccggac    420
ggcgcagggg ccgccgcggc agccgcggcc gcggccgccg cggcctggga cacgctcaag    480
atcagccagg cgccgcaggt gagcatcagc cgcagcaagt cgtaccgcga aacggggcg     540 cccttcgtgc cgccgccgcc cgcgctggac gagctgggcg gccgggggg cgtcacgcac     600 ccggaggagc gcctcggcgt ggccggcggc ccgggcagcg ccccggctgc gggtggtggc    660
accggcaccg aggacgacga ggaggagctg ctggaggacg aagaagatga ggacgaggaa    720
gaggaactgc tggaggacga cgaggaggag ctgctggagg acgacgcccg cgcgctgctc    780
aaggagcccc ggcgctgtcc tgtggccgcc actggcgccg tggccgcagc agctgccgct    840
gcagtggcca cagagggcgg ggagctgtca cccaaggagg agctgctgct gcacccggaa    900
gacgctgagg gcaaggacgg cgaggacagc gtgtgcctct ctgcgggcag cgactcggag    960
gaggggctgc tgaaacgcaa acagaggcgc taccgcacca cgttcaccag ctaccagctg   1020
gaggaactgg agcgggcctt ccagaagacg cactacctgg acgtcttcac cagggaggaa   1080
ctggccatga ggctggactt gaccgaggcc cgagtccagg tctggttcca gaaccgtcgg   1140
gccaagtggc gcaagcggga aaggcaggc gcgcagaccc accccctgg gctgcccttc     1200 ccggggccgc tctccgccac ccacccgctc agcccctacc tggacgccag ccccttccct   1260
ccgcaccacc cggcgctcga ctccgcttgg actgccgctg ccgccgccgc cgccgccgcc   1320
ttcccgagcc tacctccgcc tccgggctcg gccagcctgc cgcccagcgg ggcgccgctg   1380
ggcctgagca ctttcctcgg agcggcagtg ttccgacacc cagctttcat cagcccggca   1440
ttcggcaggc tcttttccac aatggccccc ctgaccagcg cgtcgaccgc ggccgcgctc   1500
ctgagacagc ccacacccgc cgtggagggc gcagtggcat cgggcgccct ggccgacccg   1560
gccacggcgg ccgcagacag acgcgcctct agcatagccg cgctgaggct caaggccaag   1620
gagcacgcgg cgcagctcac gcagctcaac atcctgccgg gcaccagcac gggcaaggag   1680
gtgtgctaa                                                           1689
```

<210> SEQ ID NO 8
<211> LENGTH: 569
<212> TYPE: PRT
<213> ORGANISM: Homo sapiens

<400> SEQUENCE: 8

```
Met Ser Asn Gln Tyr Gln Glu Glu Gly Cys Ser Glu Arg Pro Glu Cys
 1               5                  10                  15

Lys Ser Lys Ser Pro Thr Leu Leu Ser Ser Tyr Cys Ile Asp Ser Ile
            20                  25                  30

Leu Gly Arg Arg Ser Pro Cys Lys Met Arg Leu Leu Gly Ala Ala Gln
        35                  40                  45

Ser Leu Pro Ala Pro Leu Thr Ser Arg Ala Asp Pro Glu Lys Ala Val
    50                  55                  60

Gln Gly Ser Pro Lys Ser Ser Ser Ala Pro Phe Glu Ala Glu Leu His
65                  70                  75                  80

Leu Pro Pro Lys Leu Arg Arg Leu Tyr Gly Pro Gly Gly Gly Arg Leu
                85                  90                  95

Leu Gln Gly Ala Ala Ala Ala Ala Ala Ala Ala Ala Ala Ala Ala Ala
            100                 105                 110

Ala Ala Ala Ala Ala Ala Ala Ala Thr Ala Thr Ala Gly Pro
        115                 120                 125

Arg Gly Glu Ala Pro Pro Pro Pro Pro Thr Ala Arg Pro Gly Glu
    130                 135                 140
```

```
Arg Pro Asp Gly Ala Gly Ala Ala Ala Ala Ala Ala Ala Ala Ala Ala
145                 150                 155                 160

Ala Ala Trp Asp Thr Leu Lys Ile Ser Gln Ala Pro Gln Val Ser Ile
                165                 170                 175

Ser Arg Ser Lys Ser Tyr Arg Glu Asn Gly Ala Pro Phe Val Pro Pro
            180                 185                 190

Pro Pro Ala Leu Asp Glu Leu Gly Gly Pro Gly Gly Val Thr His Pro
            195                 200                 205

Glu Glu Arg Leu Gly Val Ala Gly Gly Pro Gly Ser Ala Pro Ala Ala
    210                 215                 220

Gly Gly Gly Thr Gly Thr Glu Asp Asp Glu Glu Leu Leu Glu Asp
225                 230                 235                 240

Glu Glu Asp Glu Asp Glu Glu Glu Leu Leu Glu Asp Asp Glu Glu
                245                 250                 255

Glu Leu Leu Glu Asp Asp Ala Arg Ala Leu Leu Lys Glu Pro Arg Arg
        260                 265                 270

Cys Pro Val Ala Ala Thr Gly Ala Val Ala Ala Ala Ala Ala Ala Ala
            275                 280                 285

Val Ala Thr Glu Gly Gly Glu Leu Ser Pro Lys Glu Glu Leu Leu Leu
    290                 295                 300

His Pro Glu Asp Ala Glu Gly Lys Asp Gly Glu Asp Ser Val Cys Leu
305                 310                 315                 320

Ser Ala Gly Ser Asp Ser Glu Glu Gly Leu Leu Lys Arg Lys Gln Arg
                325                 330                 335

Arg Tyr Arg Thr Thr Phe Thr Ser Tyr Gln Leu Glu Glu Leu Glu Arg
                340                 345                 350

Ala Phe Gln Lys Thr His Tyr Pro Asp Val Phe Thr Arg Glu Glu Leu
            355                 360                 365

Ala Met Arg Leu Asp Leu Thr Glu Ala Arg Val Gln Val Trp Phe Gln
    370                 375                 380

Asn Arg Arg Ala Lys Trp Arg Lys Arg Glu Lys Ala Gly Ala Gln Thr
385                 390                 395                 400

His Pro Pro Gly Leu Pro Phe Pro Gly Pro Leu Ser Ala Thr His Pro
                405                 410                 415

Leu Ser Pro Tyr Leu Asp Ala Ser Pro Phe Pro Pro His His Pro Ala
            420                 425                 430

Leu Asp Ser Ala Trp Thr Ala Ala Ala Ala Ala Ala Ala Ala Phe
    435                 440                 445

Pro Ser Leu Pro Pro Pro Gly Ser Ala Ser Leu Pro Pro Ser Gly
450                 455                 460

Ala Pro Leu Gly Leu Ser Thr Phe Leu Gly Ala Ala Val Phe Arg His
465                 470                 475                 480

Pro Ala Phe Ile Ser Pro Ala Phe Gly Arg Leu Phe Ser Thr Met Ala
                485                 490                 495

Pro Leu Thr Ser Ala Ser Thr Ala Ala Ala Leu Leu Arg Gln Pro Thr
            500                 505                 510

Pro Ala Val Glu Gly Ala Val Ala Ser Gly Ala Leu Ala Asp Pro Ala
    515                 520                 525

Thr Ala Ala Ala Asp Arg Arg Ala Ser Ser Ile Ala Ala Leu Arg Leu
530                 535                 540

Lys Ala Lys Glu His Ala Ala Gln Leu Thr Gln Leu Asn Ile Leu Pro
545                 550                 555                 560

Gly Thr Ser Thr Gly Lys Glu Val Cys
```

<210> SEQ ID NO 9
<211> LENGTH: 570
<212> TYPE: PRT
<213> ORGANISM: Homo sapiens

<400> SEQUENCE: 9

```
Met Ser Asn Gln Tyr Gln Glu Glu Gly Cys Ser Glu Arg Pro Glu Cys
 1               5                  10                  15

Lys Ser Lys Ser Pro Thr Leu Leu Ser Ser Tyr Cys Ile Asp Ser Ile
            20                  25                  30

Leu Gly Arg Arg Ser Pro Cys Lys Met Arg Leu Leu Gly Ala Ala Gln
        35                  40                  45

Ser Leu Pro Ala Pro Leu Thr Ser Arg Ala Asp Pro Glu Lys Ala Val
 50                  55                  60

Gln Gly Ser Pro Lys Ser Ser Ala Pro Phe Glu Ala Glu Leu His
65                  70                  75                  80

Leu Pro Pro Lys Leu Arg Arg Leu Tyr Gly Pro Gly Gly Arg Leu
                85                  90                  95

Leu Gln Gly Ala Ala Ala Ala Ala Ala Ala Ala Ala Ala Ala Ala
            100                 105                 110

Ala Ala Ala Thr Ala Thr Ala Gly Pro Arg Gly Glu Ala Pro Pro Pro
        115                 120                 125

Pro Pro Pro Thr Ala Arg Pro Gly Glu Arg Pro Asp Gly Ala Gly Ala
130                 135                 140

Ala Ala Ala Ala Ala Ala Ala Ala Ala Ala Ala Ala Ala Ala Ala Ala
145                 150                 155                 160

Ala Ala Ala Trp Asp Thr Leu Lys Ile Ser Gln Ala Pro Gln Val Ser
                165                 170                 175

Ile Ser Arg Ser Lys Ser Tyr Arg Glu Asn Gly Ala Pro Phe Val Pro
            180                 185                 190

Pro Pro Pro Ala Leu Asp Glu Leu Gly Gly Pro Gly Gly Val Thr His
        195                 200                 205

Pro Glu Glu Arg Leu Gly Val Ala Gly Gly Pro Gly Ser Ala Pro Ala
    210                 215                 220

Ala Gly Gly Gly Thr Gly Thr Glu Asp Glu Glu Glu Leu Leu Glu
225                 230                 235                 240

Asp Glu Glu Asp Glu Asp Glu Glu Leu Leu Glu Asp Asp Glu
                245                 250                 255

Glu Glu Leu Leu Glu Asp Asp Ala Arg Ala Leu Leu Lys Glu Pro Arg
            260                 265                 270

Arg Cys Pro Val Ala Ala Thr Gly Ala Val Ala Ala Ala Ala Ala
        275                 280                 285

Ala Val Ala Thr Glu Gly Gly Glu Leu Ser Pro Lys Glu Glu Leu Leu
    290                 295                 300

Leu His Pro Glu Asp Ala Glu Gly Lys Asp Gly Glu Asp Ser Val Cys
305                 310                 315                 320

Leu Ser Ala Gly Ser Asp Ser Glu Glu Gly Leu Leu Lys Arg Lys Gln
                325                 330                 335

Arg Arg Tyr Arg Thr Thr Phe Ser Tyr Gln Leu Glu Glu Leu Glu
            340                 345                 350

Arg Ala Phe Gln Lys Thr His Tyr Pro Asp Val Phe Thr Arg Glu Glu
        355                 360                 365

Leu Ala Met Arg Leu Asp Leu Thr Glu Ala Arg Val Gln Val Trp Phe
```

```
                    370                 375                 380
Gln Asn Arg Arg Ala Lys Trp Arg Lys Arg Glu Lys Ala Gly Ala Gln
385                 390                 395                 400

Thr His Pro Pro Gly Leu Pro Phe Pro Gly Pro Leu Ser Ala Thr His
                405                 410                 415

Pro Leu Ser Pro Tyr Leu Asp Ala Ser Pro Phe Pro His His Pro
                420                 425                 430

Ala Leu Asp Ser Ala Trp Thr Ala Ala Ala Ala Ala Ala Ala Ala
                435                 440                 445

Phe Pro Ser Leu Pro Pro Pro Gly Ser Ala Ser Leu Pro Pro Ser
            450                 455                 460

Gly Ala Pro Leu Gly Leu Ser Thr Phe Leu Gly Ala Ala Val Phe Arg
465                 470                 475                 480

His Pro Ala Phe Ile Ser Pro Ala Phe Gly Arg Leu Phe Ser Thr Met
                485                 490                 495

Ala Pro Leu Thr Ser Ala Ser Thr Ala Ala Leu Leu Arg Gln Pro
            500                 505                 510

Thr Pro Ala Val Glu Gly Ala Val Ala Ser Gly Ala Leu Ala Asp Pro
            515                 520                 525

Ala Thr Ala Ala Ala Asp Arg Arg Ala Ser Ser Ile Ala Ala Leu Arg
            530                 535                 540

Leu Lys Ala Lys Glu His Ala Ala Gln Leu Thr Gln Leu Asn Ile Leu
545                 550                 555                 560

Pro Gly Thr Ser Thr Gly Lys Glu Val Cys
                565                 570

<210> SEQ ID NO 10
<211> LENGTH: 482
<212> TYPE: PRT
<213> ORGANISM: Homo sapiens

<400> SEQUENCE: 10

Met Ser Asn Gln Tyr Gln Glu Glu Gly Cys Ser Glu Arg Pro Glu Cys
 1               5                  10                  15

Lys Ser Lys Ser Pro Thr Leu Leu Ser Ser Tyr Cys Ile Asp Ser Ile
                20                  25                  30

Leu Gly Arg Arg Ser Pro Cys Lys Met Arg Leu Leu Gly Ala Ala Gln
            35                  40                  45

Ser Leu Pro Ala Pro Leu Thr Ser Arg Ala Asp Pro Glu Lys Ala Val
50                  55                  60

Gln Gly Ser Pro Lys Ser Ser Ala Pro Phe Glu Ala Glu Leu His
65                  70                  75                  80

Leu Pro Pro Lys Leu Arg Arg Leu Tyr Gly Pro Gly Gly Gly Arg Leu
                85                  90                  95

Leu Gln Gly Ala Ala Ala Ala Ala Ala Ala Ala Ala Ala Ala Ala
            100                 105                 110

Ala Ala Ala Thr Ala Thr Ala Gly Pro Arg Gly Glu Ala Pro Pro
            115                 120                 125

Pro Pro Pro Thr Ala Arg Pro Gly Glu Arg Pro Asp Gly Ala Gly Ala
            130                 135                 140

Ala Ala Ala Ala Ala Ala Ala Ala Ala Trp Asp Thr Leu Lys
145                 150                 155                 160

Ile Ser Gln Ala Pro Gln Val Ser Ile Ser Arg Ser Lys Ser Tyr Arg
                165                 170                 175

Glu Asn Gly Ala Pro Phe Val Pro Pro Pro Ala Leu Asp Glu Leu
```

```
                    180                 185                 190
Gly Gly Pro Gly Gly Val Thr His Pro Glu Glu Arg Leu Gly Val Ala
                195                 200                 205
Gly Gly Pro Gly Ser Ala Pro Ala Ala Gly Gly Thr Gly Thr Glu
            210                 215                 220
Asp Asp Glu Glu Glu Leu Leu Glu Asp Glu Asp Glu Asp Glu Glu
225                 230                 235                 240
Glu Glu Leu Leu Glu Asp Glu Glu Glu Leu Leu Glu Asp Asp Ala
                245                 250                 255
Arg Ala Leu Leu Lys Glu Pro Arg Arg Cys Pro Val Ala Ala Thr Gly
            260                 265                 270
Ala Val Ala Ala Ala Ala Ala Ala Val Ala Thr Glu Gly Gly Glu
            275                 280                 285
Leu Ser Pro Lys Glu Glu Leu Leu His Pro Glu Asp Ala Glu Gly
        290                 295                 300
Lys Asp Gly Glu Asp Ser Val Cys Leu Ser Ala Gly Ser Asp Ser Glu
305                 310                 315                 320
Glu Gly Leu Leu Lys Arg Lys Gln Arg Arg Tyr Arg Thr Thr Phe Thr
                325                 330                 335
Ser Tyr Gln Leu Glu Glu Leu Glu Arg Ala Phe Gln Lys Thr His Tyr
            340                 345                 350
Pro Asp Val Phe Thr Arg Glu Glu Leu Ala Met Arg Leu Asp Leu Thr
        355                 360                 365
Glu Ala Arg Val Gln Val Trp Phe Gln Asn Arg Arg Ala Lys Trp Arg
    370                 375                 380
Lys Arg Glu Lys Ala Gly Ala Gln Thr His Pro Pro Gly Leu Pro Phe
385                 390                 395                 400
Pro Gly Pro Leu Ser Ala Thr His Pro Leu Ser Pro Tyr Leu Asp Ala
                405                 410                 415
Ser Pro Phe Pro Pro His His Pro Ala Leu Asp Ser Ala Trp Thr Ala
            420                 425                 430
Ala Ala Ala Ala Ala Ala Ala Ala Phe Pro Ser Leu Pro Pro Pro
        435                 440                 445
Gly Ser Ala Ser Leu Pro Pro Ser Gly Ala Pro Leu Gly Leu Ser Thr
    450                 455                 460
Phe Leu Gly Ala Ala Val Phe Arg His Pro Ala Phe Ile Ser Pro Ala
465                 470                 475                 480
Phe Gly

<210> SEQ ID NO 11
<211> LENGTH: 562
<212> TYPE: PRT
<213> ORGANISM: Homo sapiens

<400> SEQUENCE: 11

Met Ser Asn Gln Tyr Gln Glu Glu Gly Cys Ser Glu Arg Pro Glu Cys
1               5                   10                  15
Lys Ser Lys Ser Pro Thr Leu Leu Ser Ser Tyr Cys Ile Asp Ser Ile
                20                  25                  30
Leu Gly Arg Arg Ser Pro Cys Lys Met Arg Leu Leu Gly Ala Ala Gln
            35                  40                  45
Ser Leu Pro Ala Pro Leu Thr Ser Arg Ala Asp Pro Glu Lys Ala Val
    50                  55                  60
Gln Gly Ser Pro Lys Ser Ser Ser Ala Pro Phe Glu Ala Glu Leu His
65                  70                  75                  80
```

```
Leu Pro Pro Lys Leu Arg Arg Leu Tyr Gly Pro Gly Gly Arg Leu
            85                  90                  95

Leu Gln Gly Ala Ala Ala Ala Ala Ala Ala Ala Ala Ala Ala Ala
            100                 105                 110

Ala Ala Ala Thr Ala Thr Ala Gly Pro Arg Gly Glu Ala Pro Pro
            115                 120                 125

Pro Pro Pro Thr Ala Arg Pro Gly Glu Arg Pro Asp Gly Ala Gly Ala
130                 135                 140

Ala Ala Ala Ala Ala Ala Ala Ala Ala Ala Trp Asp Thr Leu Lys
145                 150                 155                 160

Ile Ser Gln Ala Pro Gln Val Ser Ile Ser Arg Ser Lys Ser Tyr Arg
                165                 170                 175

Glu Asn Gly Ala Pro Phe Val Pro Pro Pro Ala Leu Asp Glu Leu
            180                 185                 190

Gly Gly Pro Gly Gly Val Thr His Pro Glu Glu Arg Leu Gly Val Ala
            195                 200                 205

Gly Gly Pro Gly Ser Ala Pro Ala Ala Gly Gly Thr Gly Thr Glu
            210                 215                 220

Asp Asp Glu Glu Glu Leu Leu Glu Asp Glu Asp Glu Asp Glu Glu
225                 230                 235                 240

Glu Glu Leu Leu Glu Asp Asp Glu Glu Glu Leu Leu Glu Asp Asp Ala
                245                 250                 255

Arg Ala Leu Leu Lys Glu Pro Arg Arg Cys Pro Val Ala Ala Thr Gly
                260                 265                 270

Ala Val Ala Ala Ala Ala Ala Ala Val Ala Thr Glu Gly Gly Glu
            275                 280                 285

Leu Ser Pro Lys Glu Glu Leu Leu Leu His Pro Glu Asp Ala Glu Gly
                290                 295                 300

Lys Asp Gly Glu Asp Ser Val Cys Leu Ser Ala Gly Ser Asp Ser Glu
305                 310                 315                 320

Glu Gly Leu Leu Lys Arg Lys Gln Arg Arg Tyr Arg Thr Thr Phe Thr
                325                 330                 335

Ser Tyr Gln Leu Glu Glu Leu Glu Arg Ala Phe Gln Lys Thr His Tyr
                340                 345                 350

Leu Asp Val Phe Thr Arg Glu Glu Leu Ala Met Arg Leu Asp Leu Thr
                355                 360                 365

Glu Ala Arg Val Gln Val Trp Phe Gln Asn Arg Arg Ala Lys Trp Arg
                370                 375                 380

Lys Arg Glu Lys Ala Gly Ala Gln Thr His Pro Pro Gly Leu Pro Phe
385                 390                 395                 400

Pro Gly Pro Leu Ser Ala Thr His Pro Leu Ser Pro Tyr Leu Asp Ala
                405                 410                 415

Ser Pro Phe Pro Pro His His Pro Ala Leu Asp Ser Ala Trp Thr Ala
                420                 425                 430

Ala Ala Ala Ala Ala Ala Ala Phe Pro Ser Leu Pro Pro Pro
                435                 440                 445

Gly Ser Ala Ser Leu Pro Pro Ser Gly Ala Pro Leu Gly Leu Ser Thr
                450                 455                 460

Phe Leu Gly Ala Ala Val Phe Arg His Pro Ala Phe Ile Ser Pro Ala
465                 470                 475                 480

Phe Gly Arg Leu Phe Ser Thr Met Ala Pro Leu Thr Ser Ala Ser Thr
                485                 490                 495

Ala Ala Ala Leu Leu Arg Gln Pro Thr Pro Ala Val Glu Gly Ala Val
```

```
                        500                 505                 510
Ala Ser Gly Ala Leu Ala Asp Pro Ala Thr Ala Ala Asp Arg Arg
        515                 520                 525

Ala Ser Ser Ile Ala Ala Leu Arg Leu Lys Ala Lys Glu His Ala Ala
        530                 535                 540

Gln Leu Thr Gln Leu Asn Ile Leu Pro Gly Thr Ser Thr Gly Lys Glu
545                 550                 555                 560

Val Cys

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
gctcactaca cttgttaccg c                                         21

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
aattgacaat tccaggccac tg                                        22

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
acgcctgggc ctaggcactg                                           20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
ctcggtgccg gtgccaccac                                           20

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
gcaagtcgta ccgcgagaac g                                         21

<210> SEQ ID NO 17
<211> LENGTH: 20
<212> TYPE: DNA
<213> ORGANISM: Artificial Sequence
<220> FEATURE:
<223> OTHER INFORMATION: primer
```

```
<400> SEQUENCE: 17
tgcgctctct gccgctgcga                                          20

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18
gaaatagctg agagggcatt gc                                       22

<210> SEQ ID NO 19
<211> LENGTH: 23
<212> TYPE: DNA
<213> ORGANISM: Artificial Sequence
<220> FEATURE:
<223> OTHER INFORMATION: primer

<400> SEQUENCE: 19
tctcttggtt ttgtgaaggg gat                                      23

<210> SEQ ID NO 20
<211> LENGTH: 23
<212> TYPE: DNA
<213> ORGANISM: Artificial Sequence
<220> FEATURE:
<223> OTHER INFORMATION: primer

<400> SEQUENCE: 20
gacgcgtccg aaaacaacct gag                                      23

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
ccccagcctc tgtgtgtatg                                          20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
acagctcccg aggccatgac                                          20

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
gagtggtgct gagtgaggtg a                                        21

<210> SEQ ID NO 24
<211> LENGTH: 20
```

-continued

```
<212> TYPE: DNA
<213> ORGANISM: Artificial Sequence
<220> FEATURE:
<223> OTHER INFORMATION: primer

<400> SEQUENCE: 24
gcgagggccc cagcgtgaag                                                  20

<210> SEQ ID NO 25
<211> LENGTH: 21
<212> TYPE: DNA
<213> ORGANISM: Artificial Sequence
<220> FEATURE:
<223> OTHER INFORMATION: primer

<400> SEQUENCE: 25
gcctgtatgg agcattcaca c                                                21

<210> SEQ ID NO 26
<211> LENGTH: 2721
<212> TYPE: DNA
<213> ORGANISM: Homo sapiens

<400> SEQUENCE: 26
tccatcccac cctccgggag aggcagccgg cgatccgctc tctgcgccct gggaaaaagc        60
cccagccatg agcaatcagt accaggagga gggctgctcc gagaggcccg agtgcaaaag       120
taaatctcca actttgctct cctcctactg catcgacagc atcctgggcc ggaggagccc       180
gtgcaaaatg cggttgctgg agccgcgca gagcttgcct gctccgctga ccagccgcgc        240
cgacccggaa aaggccgtgc aaggctcccc taagagcagc agcgccccgt cgaggccga        300 gctgcacctg ccgcccaagc tgcggcgcct gtacggcccg gcgggggcc gcctccttca        360 gggtgcggca gcggcggcgg cggcggcggc ggcggcggcg gcagcggccg ccacggccac        420
ggcgggtcca cgcggggagg cccctccgcc gccaccgcca accgcgcggc ccggggaacg       480
gccggacggc gcaggggccg ccgcggcagc cgcggccgcg ccgccgcgg cctgggacac        540 gctcaagatc agccaggcgc cgcaggtgag catcagccgc agcaagtcgt accgcgagaa       600
cggggcgccc ttcgtgccgc cgccgcccgc gctggacgag ctgggcggcc cggggggcgt       660
cacgcacccg gaggagcgcc tcggcgtggc cggcggcccg ggcagcgccc cggctgcggg       720
tggtggcacc ggcaccgagg acgacgagga ggagctgctg gaggacgaag aagatgagga       780
cgaggaagag gaactgctgg aggacgacga ggaggagctg ctggaggacg acgcccgcgc       840
gctgctcaag gagccccggc gctgtcctgt ggccgccact ggcgccgtgg ccgcagcagc       900
tgccgctgca gtggccacag agggcgggga gctgtcaccc aaggaggagc tgctgctgca       960
cccggaagac gctgagggca aggacggcga ggacagcgtg tgcctctctg cgggcagcga     1020
ctcggaggag gggctgctga acgcaaaca gaggcgctac cgcaccacgt tcaccagcta     1080
ccagctggag gaactggagc gggccttcca gaagacgcac taccggacg tcttcaccag     1140 ggaggaactg gccatgaggc tggacttgac cgaggcccga gtccaggtct ggttccagaa     1200
ccgtcgggcc aagtggcgca gcggagaa ggcaggcgcg cagacccacc ccctgggct     1260 gcccttcccg gggccgctct ccgccaccca ccctcagc cctacctgg acgccagccc     1320 cttccctccg caccacccgg cgctcgactc gcttggact gccgctgccg ccgccgcgc     1380 cgccgccttc ccgagcctac ctccgcctcc gggctcggcc agcctgccgc ccagcggggc     1440
gccgctgggc ctgagcactt tcctcggagc ggcagtgttc cgacacccag ctttcatcag     1500
cccggcattc ggcaggctct tttccacaat ggccccctg accagcgcgt cgaccgcggc     1560
```

```
cgcgctcctg agacagccca cacccgccgt ggagggcgca gtggcatcgg gcgccctggc    1620
cgacccggcc acggcggccg cagacagacg cgcctctagc atagccgcgc tgaggctcaa    1680
ggccaaggag cacgcggcgc agctcacgca gctcaacatc ctgccgggca ccagcacggg    1740
caaggaggtg tgctaaaggc tgccctccac acccgcgccc cgcgcgcgcc ccgaaaggtc    1800
acctcactca gcaccactca agaccaaatg gaaacagagg accagcacac tcccgagacg    1860
gcactgagag agcgcagccg ccttcacagc agtctggatg cgggcatggc agccctcggc    1920
gctccgggac gtggcacctc ctcggctggc tgtccacccg ccctgcccc tgcccctgct     1980 actgccaacc tcgctccaac tccaacatcc actctctctt gttcttactt tcctgaaaat    2040
atcggggagg ttttctcccc cagacgcctg atattgaagt aaaaaattta aaaagcccaa    2100
cctcttcctc ctgacacccc acttagcctt tcttttcttc tttctttctt tctttttttt    2160
ttttaaatag cattttggcg ctcgaagttg atctccccag cgagggcccc agcgtgaagc    2220
cagggcccgg gaagcaaatg cgagcctgta agatagctaa cagtgcactt aaaggaaagg    2280
ggcgtcttgt tcttgttctc ttctttatca tacaccaacc aaggttttta tatcaaacca    2340
aagggaaata atactctgct agaatatgga ctgttgaagt caccaaactg tgattattga    2400
ttctgtacat accattgtta ttaaaaaaaa aaaaaaaaga acagagcttt gtatatttga    2460
aatgttataa cgcaattgca ctcagcgtgg tatggtaaaa gtttgtcctc ccgtagattc    2520
ttactgtgtt gtagatacgg tagggttcct agacaaatat ttatgtactc aagccccttta   2580 tttaacttat taactgtaga ggcttccgaa accttcaaga taaaggcaat ggtacagtac    2640
ttttgtgtaa tgtgtaattg ttaccacttt tccttgctat ctagtggaga agtgtcacgc    2700
tcaaaataaa aaaattatat g                                               2721

<210> SEQ ID NO 27
<211> LENGTH: 34
<212> TYPE: DNA
<213> ORGANISM: Homo sapiens

<400> SEQUENCE: 27
ggcggcggca gcggccgcca cggccacggc gggt                                 34

<210> SEQ ID NO 28
<211> LENGTH: 11
<212> TYPE: PRT
<213> ORGANISM: Homo sapiens

<400> SEQUENCE: 28

Ala Ala Ala Ala Ala Ala Thr Ala Thr Ala Gly
1               5                   10

<210> SEQ ID NO 29
<211> LENGTH: 55
<212> TYPE: DNA
<213> ORGANISM: Homo sapiens

<400> SEQUENCE: 29
ggcggcggcg gcggcggcgg cggcggcggc agcggccgcc acggccacgg cgggt          55

<210> SEQ ID NO 30
<211> LENGTH: 18
<212> TYPE: PRT
<213> ORGANISM: Homo sapiens

<400> SEQUENCE: 30
```

```
Ala Ala Ala Ala Ala Ala Ala Ala Ala Ala Ala Thr Ala Thr
1               5                   10                  15

Ala Gly

<210> SEQ ID NO 31
<211> LENGTH: 33
<212> TYPE: DNA
<213> ORGANISM: Homo sapiens

<400> SEQUENCE: 31 gggggccgccg cggcagccgc ggccgcggcc gcc                              33

<210> SEQ ID NO 32
<211> LENGTH: 11
<212> TYPE: PRT
<213> ORGANISM: Homo sapiens

<400> SEQUENCE: 32

Gly Ala Ala Ala Ala Ala Ala Ala Ala Ala Ala
1               5                   10

<210> SEQ ID NO 33
<211> LENGTH: 57
<212> TYPE: DNA
<213> ORGANISM: Homo sapiens

<400> SEQUENCE: 33
ggggccgccg cggcagccgc ggccgcggcc gccgcggcag ccgcggccgc ggccgcc     57

<210> SEQ ID NO 34
<211> LENGTH: 19
<212> TYPE: PRT
<213> ORGANISM: Homo sapiens

<400> SEQUENCE: 34

Gly Ala Ala Ala Ala Ala Ala Ala Ala Ala Ala Ala Ala Ala Ala
1               5                   10                  15

Ala Ala Ala

<210> SEQ ID NO 35
<211> LENGTH: 59
<212> TYPE: PRT
<213> ORGANISM: Homo sapiens

<400> SEQUENCE: 35

Gln Arg Arg Tyr Arg Thr Thr Phe Thr Ser Tyr Gln Leu Glu Glu Leu
1               5                   10                  15

Glu Arg Ala Phe Gln Lys Thr His Tyr Pro Asp Val Phe Thr Arg Glu
                20                  25                  30

Glu Leu Ala Met Arg Leu Asp Leu Thr Glu Ala Arg Val Gln Val Trp
            35                  40                  45

Thr Gln Asn Arg Arg Ala Lys Trp Arg Lys Arg
        50                  55

<210> SEQ ID NO 36
<211> LENGTH: 59
<212> TYPE: PRT
<213> ORGANISM: Homo sapiens

<400> SEQUENCE: 36

Gln Arg Arg Tyr Arg Thr Thr Phe Thr Ser Tyr Gln Leu Glu Glu Leu
1               5                   10                  15
```

-continued

Glu Arg Ala Phe Gln Lys Thr His Tyr Leu Asp Val Phe Thr Arg Glu
            20                  25                  30

Glu Leu Ala Met Arg Leu Asp Leu Thr Glu Ala Arg Val Gln Val Trp
        35                  40                  45

Thr Gln Asn Arg Arg Ala Lys Trp Arg Lys Arg
    50                  55

<210> SEQ ID NO 37
<211> LENGTH: 59
<212> TYPE: PRT
<213> ORGANISM: Mus Musculus

<400> SEQUENCE: 37

Gln Arg Arg Tyr Arg Thr Thr Phe Thr Ser Tyr Gln Leu Glu Glu Leu
1               5                   10                  15

Glu Arg Ala Phe Gln Lys Thr His Tyr Pro Asp Val Phe Thr Arg Glu
            20                  25                  30

Glu Leu Ala Met Arg Leu Asp Leu Thr Glu Ala Arg Val Gln Val Trp
        35                  40                  45

Thr Gln Asn Arg Arg Ala Lys Trp Arg Lys Arg
    50                  55

<210> SEQ ID NO 38
<211> LENGTH: 59
<212> TYPE: PRT
<213> ORGANISM: Stronglylocentrotus purpuratus

<400> SEQUENCE: 38

Gln Arg Arg Tyr Arg Thr Thr Phe Thr Ser Tyr Gln Leu Glu Glu Leu
1               5                   10                  15

Glu Arg Ala Phe Gln Lys Thr His Tyr Pro Asp Val Phe Thr Arg Glu
            20                  25                  30

Glu Leu Ala Met Arg Leu Asp Leu Thr Glu Ala Arg Val Gln Val Trp
        35                  40                  45

Thr Gln Asn Arg Arg Ala Lys Trp Arg Lys Arg
    50                  55

<210> SEQ ID NO 39
<211> LENGTH: 58
<212> TYPE: PRT
<213> ORGANISM: Drosophila melanogaster

<400> SEQUENCE: 39

Gln Arg Arg Tyr Arg Thr Thr Phe Thr Ser Tyr Gln Leu Glu Glu Leu
1               5                   10                  15

Glu Arg Ala Phe Cys Lys Thr His Tyr Pro Asp Val Thr Arg Glu Glu
            20                  25                  30

Leu Ala Met Arg Val Asp Leu Thr Glu Ala Arg Val Gln Val Trp Phe
        35                  40                  45

Gln Asn Arg Arg Ala Lys Trp Arg Lys Arg
    50                  55

<210> SEQ ID NO 40
<211> LENGTH: 59
<212> TYPE: PRT
<213> ORGANISM: Hydra vulgaris

<400> SEQUENCE: 40

Gln Arg Arg Tyr Arg Thr Thr Phe Thr Ser Phe Gln Leu Glu Glu Leu
1               5                   10                  15

```
Glu Lys Ala Phe Ser Arg Thr His Tyr Pro Leu Val Phe Thr Arg Glu
            20                  25                  30

Glu Leu Ala Met Lys Ile Gly Leu Thr Glu Ala Arg Leu Gln Val Trp
        35                  40                  45

Phe Gln Asn Arg Arg Ala Lys Trp Arg Lys Gln
    50                  55

<210> SEQ ID NO 41
<211> LENGTH: 58
<212> TYPE: PRT
<213> ORGANISM: Homo sapiens

<400> SEQUENCE: 41

Glu Arg Arg Tyr Arg Thr Thr Phe Thr Gln Phe Gln Leu Asp Glu Leu
1               5                   10                  15

Glu Arg Ala Phe Asp Lys Thr His Tyr Pro Asp Val Met Arg Glu Glu
            20                  25                  30

Leu Ala Val Arg Val His Leu Thr Glu Ala Arg Val Gln Val Trp Phe
        35                  40                  45

Gln Asn Arg Arg Ala Lys Trp Arg Lys Arg
    50                  55

<210> SEQ ID NO 42
<211> LENGTH: 59
<212> TYPE: PRT
<213> ORGANISM: Homo sapiens

<400> SEQUENCE: 42

Gln Lys Arg His Arg Thr Arg Phe Thr Pro Ala Gln Leu Asn Glu Leu
1               5                   10                  15

Glu Arg Ser Phe Ala Lys Thr His Tyr Pro Asp Ile Phe Met Arg Glu
            20                  25                  30

Glu Leu Ala Leu Arg Ile Gly Leu Thr Glu Ser Arg Val Gln Val Trp
        35                  40                  45

Phe Gln Asn Arg Arg Ala Lys Trp Lys Lys Arg
    50                  55

<210> SEQ ID NO 43
<211> LENGTH: 59
<212> TYPE: PRT
<213> ORGANISM: Homo sapiens

<400> SEQUENCE: 43

Gln Arg Arg Ser Arg Thr Asn Phe Thr Leu Glu Gln Leu Asn Glu Leu
1               5                   10                  15

Glu Arg Leu Phe Asp Glu Thr His Tyr Pro Ile Ala Phe Met Arg Glu
            20                  25                  30

Glu Leu Ser Gln Arg Leu Gly Leu Ser Glu Ala Arg Val Gln Val Trp
        35                  40                  45

Ile Gln Asn Arg Arg Ala Lys Cys Arg Lys Gln
    50                  55

<210> SEQ ID NO 44
<211> LENGTH: 60
<212> TYPE: PRT
<213> ORGANISM: Homo sapiens

<400> SEQUENCE: 44

Lys Arg Arg Asn Arg Thr Thr Phe Ser Thr Phe Gln Leu Glu Glu Leu
1               5                   10                  15
```

Glu Lys Val Phe Gln Lys Thr His Tyr Pro Asp Val Tyr Ala Arg Glu
            20                  25                  30

Glu Gln Leu Ala Leu Arg Thr Asp Leu Thr Glu Ala Arg Val Gln Val
        35                  40                  45

Trp Phe Gln Asn Arg Arg Ala Lys Trp Arg Lys Arg
    50                  55                  60

<210> SEQ ID NO 45
<211> LENGTH: 60
<212> TYPE: PRT
<213> ORGANISM: Homo sapiens

<400> SEQUENCE: 45

Lys Arg Arg Asn Arg Thr Thr Phe Thr Ser Tyr Gln Leu Glu Glu Leu
1               5                   10                  15

Glu Lys Val Phe Gln Lys Thr His Tyr Pro Asp Val Tyr Ala Arg Glu
            20                  25                  30

Glu Gln Leu Ala Met Arg Thr Asp Leu Thr Glu Ala Arg Val Gln Val
        35                  40                  45

Trp Phe Gln Asn Arg Arg Ala Lys Trp Arg Lys Arg
    50                  55                  60

<210> SEQ ID NO 46
<211> LENGTH: 58
<212> TYPE: PRT
<213> ORGANISM: Homo sapiens

<400> SEQUENCE: 46

His Arg Arg Asn Arg Thr Thr Phe Thr Thr Tyr Gln Leu His Glu Leu
1               5                   10                  15

Glu Arg Ala Phe Glu Lys Ser His Tyr Pro Asp Tyr Ser Arg Glu Leu
            20                  25                  30

Leu Ala Gly Lys Val Asn Leu Pro Glu Val Arg Val Gln Val Trp Phe
        35                  40                  45

Gln Asn Arg Arg Ala Lys Trp Arg Arg Gln
    50                  55

<210> SEQ ID NO 47
<211> LENGTH: 58
<212> TYPE: PRT
<213> ORGANISM: Homo sapiens

<400> SEQUENCE: 47

Gln Arg Arg Gln Arg Thr His Phe Thr Ser Gln Gln Leu Gln Glu Leu
1               5                   10                  15

Glu Ala Thr Phe Gln Arg Asn Arg Tyr Asp Met Ser Met Arg Glu Glu
            20                  25                  30

Ile Ala Val Trp Thr Asn Leu Ile Glu Pro Arg Val Arg Val Trp Ile
        35                  40                  45

Lys Asn Arg Arg Ala Lys Trp Arg Lys Arg
    50                  55

<210> SEQ ID NO 48
<211> LENGTH: 8
<212> TYPE: PRT
<213> ORGANISM: Homo sapiens

<400> SEQUENCE: 48

Pro Pro Lys Leu Arg Arg Leu Tyr
1               5

HOMEOBOX GENE

RELATED APPLICATIONS

This application is the U.S. National Stage of International Application No. PCT/AU02/01599, filed Nov. 26, 2002, published in English, and claims priority under 35 U.S.C. §119 or 365 to Australian Application No. PR9095, filed Nov. 26, 2001.

TECHNICAL FIELD

The present invention relates to a novel homeobox gene, the human ortholog of the Aristaless homeobox gene, ARX. The ARX gene has been associated with infantile spasms but, in addition, has been associated with non-specific X-linked mental retardation, X-linked myoclonic epilepsy and Partington syndrome. In view of the realisation that the ARX gene plays a role in these conditions, the mutations responsible have been identified and may be used in their diagnosis.

BACKGROUND ART

Infantile spasms (IS) are a particular form of seizure, usually confined to infancy and often associated with mental retardation. Where IS are associated with hypsarrhythmia (a chaotic brain wave pattern) on electroencephalogram (EEG) and developmental arrest, the term West syndrome is used. IS are often symptomatic of a heterogeneous group of aetiologies such as structural brain malformations or brain injury. A rare subgroup of IS is due to genetic factors (idiopathic IS) and generally has a better prognosis than the symptomatic group. A subgroup of IS is X-linked IS which carries a poor prognosis (ISSX, MIM 308350). The ISSX family of Bruyere et al. initially defined the candidate ISSX gene region to ~7 Mb, between DXS1226 and AHC (Adrenal Hypoplasia Congenital).

DISCLOSURE OF THE INVENTION

The present invention relates to the human ortholog of the Aristaless homeobox gene, ARX.

According to one aspect of the present invention there is provided an isolated DNA molecule comprising the nucleotide sequence set forth in SEQ ID NO:1, this being the ORF identified in FIG. 1b. The polypeptide encoded by the gene contains a homeobox domain encompassing amino acid residues 327-386 as shown in FIG. 1b. As will be appreciated by the person skilled in the art, homeobox domains are very highly conserved over a wide variety of organisms. Proteins containing these types of sequences are thought to be transcription factors, and are important in the regulation of other genes and gene products. Thus, they are involved in the control of many developmental processes, including neuronal development.

The invention also encompasses an isolated DNA molecule which hybridises under stringent conditions with a DNA molecule consisting of the nucleotide sequence set forth in SEQ ID NO:1.

The invention also provides an isolated DNA molecule consisting of the nucleotide sequence set forth in SEQ ID NO:1 or SEQ ID NO:3.

Still further, the invention provides an isolated DNA molecule which encodes a polypeptide having the amino acid sequence set forth in SEQ ID NO:2.

In a further aspect, the present invention provides an isolated ARX gene comprising the nucleotide sequence set forth in FIG. 1b (SEQ ID NO:26) and appropriate control elements. These may be those naturally present in the UTR as illustrated in FIG. 1b (SEQ ID NO:26) and SEQ ID NO:3, or may be non-natural control elements such as exogenous promoters. The nucleotide sequence set forth in FIG. 1b (SEQ ID NO:26) is cDNA sequence of the human ARX gene. SEQ ID NO:3 encompasses SEQ ID NO:26 in its entirety and includes naturally present control elements upstream and downstream of SEQ ID NO:26.

According to a further aspect of the present invention, there is provided a mutant ARX whose function has been altered or destroyed.

In a preferred embodiment of the invention there is provided a mutant ARX gene comprising a mutation selected from the group consisting of:
1) an insertion of trinucleotide repeats coding for additional alanine residues within a polyalanine tract;
2) a duplication coding for additional alanine residues within a polyalanine tract;
3) a deletion; and
4) a missense mutation within the homeobox.

In a particularly preferred embodiment, the mutations are selected from the group consisting of
(i) an insertion of (GCG)$_7$ trinucleotide repeats within the first polyalanine tract;
(ii) a 24 bp duplication coding for 8 additional alanine residues in the second polyalanine tract;
(iii) a deletion encompassing exon 5; and
(iv) a 1058 C>T missense mutation,
as set forth in SEQ ID NOs:4, 5, 6 and 7, respectively, and whose expression products are shown in SEQ ID Nos:8, 9, 10 and 11.

According to a further aspect of the present invention, there is provided an isolated polypeptide comprising the amino acid sequence set forth in FIG. 1b (SEQ ID NO:2).

The invention also encompasses an isolated polypeptide having at least 70%, preferably 85% and more preferably 95% identity outside of the homeodomain with the amino acid sequence set forth in FIG. 1b (SEQ ID NO:2), and the polypeptides encoded by the mutant ARX genes described above.

Amino acid sequence variants of ARX are prepared by introducing appropriate nucleotide changes into DNA, and subsequently expressing the resulting modified DNA in a host cell, or alternatively may be prepared by in vitro synthesis. Such variants include deletions, insertions or substitutions of amino acid residues within the amino acid sequence set out in SEQ ID NO: 2. Any combination of deletion, insertion, and substitution may be made to arrive at an amino acid sequence variant of ARX, provided that the variant possesses the desired functional characteristics described herein. There are two principal variables in the construction of amino acid sequence variants of a peptide: the location of the mutation site and the nature of the mutation. In general, the location and nature of the mutation chosen will depend upon the characteristic to be modified.

For example, due to the degeneracy of nucleotide coding sequences, mutations can be made in the ARX nucleotide sequence without affecting the amino acid sequence of the product encoded by this sequence. Other mutations can be made which will result in a peptide which has an amino acid sequence different from that set out in SEQ ID NO: 2, but which is functionally active. Such functionally active amino acid sequence variants of XXXX are selected, for example, by substituting one or more amino acid residues in the amino acid sequence set out in SEQ ID NO: 2 with other amino acid residues of a similar or different polarity or charge.

In a further aspect of the present invention, there is provided a method of preparing ARX or a variant thereof as described above, comprising the steps of:

culturing host cells transformed with the DNA molecule as described above under conditions effective for the production of polypeptides; and harvesting the polypeptides.

In a still further aspect of the present invention, there is provided host cells transformed with a DNA molecule as described above.

In a still further aspect of the present invention, there is provided an animal model in which a wild-type mutant DNA molecule as described above is expressed, or the ARX gene is knocked out.

The present invention also provides a means for the diagnosis of the conditions described above. Accordingly, in a further aspect of the present invention, there is provided the use of a DNA molecule as described above or a polypeptide as described above in the diagnosis of diseases associated with mutation in the ARX gene. In particular, these molecules are useful in the correct diagnosis of infantile spasms, X-linked mental retardation, X-linked myoclonic epilepsy, Partington syndrome and dystonia. Screening of individuals without these diseases may also be conducted, particularly of relatives of affected people, in order to establish whether they carry the mutation, and pre-natal and pre-implantation testing are also envisaged.

Throughout this specification and the claims, the words "comprise", "comprises" and "comprising" are used in a non-exclusive sense, except where the context requires otherwise.

It will be clearly understood that, although a number of prior art publications are referred to herein, this reference does not constitute an admission that any of these documents forms part of the common general knowledge in the art, in Australia or in any other country.

BRIEF DESCRIPTION OF THE DRAWINGS

FIG. 1b is cDNA and protein sequence of the human ARX gene. Sequence of the ARX cDNA (SEQ ID NO:26) is shown. Untranslated regions (5'UTR-incomplete, and 3' UTR) are in lowercase letters, ORF is in uppercase letters. The numbers on the right correspond to the cDNA/ORF, as well as translated ARX protein sequence (SEQ ID NO:2) positions, respectively. Exon/exon boundaries are indicated with asterisks (*). The canonical polyadenylation signal (AATAAA) is in uppercase letters and underlined (position 2705-2709). Two homogeneous GC-rich trinucleotide repeats, $(GCG)_{10}$ and $(GCC)_7$, are boxed. Four polyA tracts are underlined with those harboring mutations boxed. The 24 by region of duplication (428-451 dup (24 bp) and 1 517-bp deletion of intron 4 and exon 5 of ARX of the small ISSX family (IVS4-816_EX5701del/483fs) are boxed. The point mutation found in the myoclonic epilepsy family (1058C>T, P313L) is highlighted by a black box within the homeodomain of the ARX protein (boxed amino acid residues 327-386, P26 residue of the homeodomain). The other two conserved domains of the paired type homoebox proteins, the octapeptide (amino acids 25-34) and the aristaless domain (amino acids 527-562) are boxed. ARX nuclear localisation sequence (NLS) PPKLRRLY (position 82-89; SEQ ID NO:48) is circled.

The FIGS. 2a-b are DNA sequence chromatograms showing ARX gene mutations affecting polyA tracts.

FIG. 3b shows part of the large pedigree of the myoclonic epilepsy family showing the co-segregation of the 1058C>T mutation with the affected status in this family. Corresponding part of exon 2 of ARX was amplified from genomic DNA and digested with the MspI restriction enzyme to distinguish between the normal (presence of 9 MspI restriction enzyme sites) and 1058C>T mutated chromosome (abolishing the most 3'-end site and thus generating a large 220-bp product instead of two 162-bp and 58-bp products-indicated with an asterisk). Sizes of the resulting restriction fragments are indicated. The primers used in this experiment are those used for genomic PCR and sequencing of exon 2 (2P2F and 2P2R, see Materials and Methods and SEQ ID NOs:16 and 17). FIG. 3c shows ClustalW alignment of the paired type homeodomain of the normal human ARX (Homo sapiens) protein (SEQ ID NO:35), the P353L mutation (SEQ ID NO:36), mouse (Arx, *Mus musculus*; SEQ ID NO:37), zebrafish (Arx, *Danio rerio*; SEQ ID NO:38), sea urchin (Arx-like, *Strongylocentrotus purpuratus*; SEQ ID NO:39), fly (A1, *Drosophila melanogaster*; SEQ ID NO:40), and polyp (prdl-a, *Hydra vulgaris*; SEQ ID NO:41) orthologs, Human DTP (SEQ ID NO:42); and other representatives of the aristaless-related proteins (e.g., SHOX (SEQ ID NO:43), ALX3 from Group I (SEQ ID NO:44); OTP (SEQ ID NO:45) and Rx (SEQ ID NO:46) from Group II (ARX is a member of this group); and PITX1 (SEQ ID NO:47) from Group III; classification according to ref.18). The invariant proline P353 residue (P26 of the homeodomain) is boxed and indicated with an arrow. On the alignment, the residues that differ from the consensus are shown on a black background. These include the P353L mutation as identified in the myoclonic epilepsy family in this study.

MODES FOR PERFORMING THE INVENTION

Figure 1A:
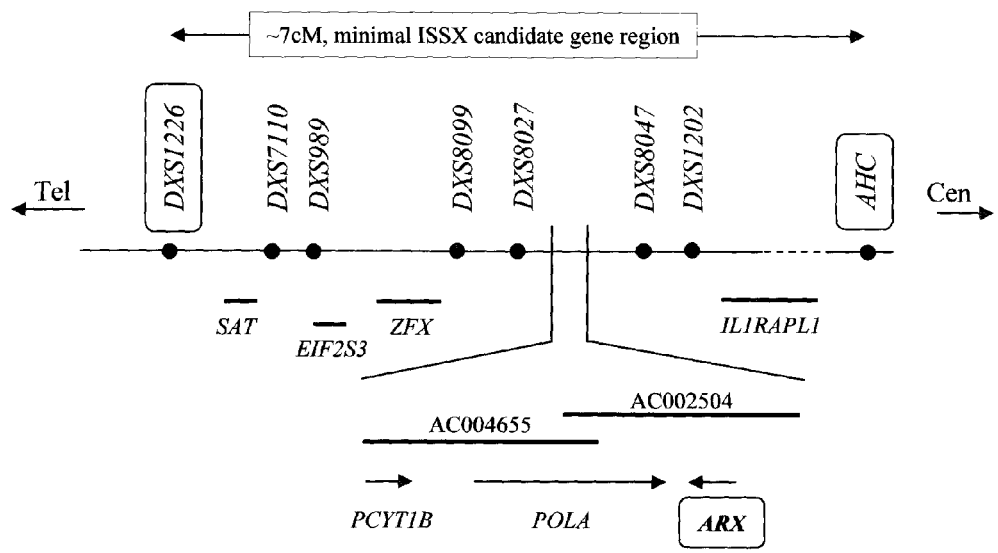
FIG. 1a is a map showing ISSX candidate gene region in Xp22. The minimal ~7cM ISSX candidate gene region between the markers DXS1226 and AHC is shown. Known genes and STS's from the region are indicated. Position and orientation of ARX with respect to the POLA gene is highlighted. GenBank accession numbers for genomic sequences for these two genes are shown. The cen-to-tel orientation of the POLA-ARX region is shown as annotated in Ensembl. The map is not drawn to scale.

Preferred embodiments of the invention will now be described, by way of example only, with reference to the Figures.

The terms "cell," "host cell," "cell line," and "cell culture" are used interchangeably, and all such terms should be understood to include progeny of the cells.

"Control sequences" refers to DNA sequences necessary for the expression of an operably linked nucleotide coding sequence in a particular host cell. Control sequences suitable for expression in prokaryotes include origins of replication, promoters, ribosome binding sites, and transcription termination sites. Control sequences suitable for expression in eukaryotes include origins of replication, promoters, ribosome binding sites, polyadenylation signals, and enhancers.

An "exogenous" element is one that is foreign to the host cell, or homologous to the host cell but in a position within the host cell in which the element is ordinarily not found.

"Polymerase chain reaction," or "PCR," as used herein generally refers to a method for amplification of a desired nucleotide sequence in vitro, as described in U.S. Pat. No. 4,683,195. In general, the PCR method involves repeated cycles of primer extension synthesis, using two oligonucleotide primers capable of hybridizing preferentially to a template nucleic acid. Typically, the primers used in the PCR method will be complementary to nucleotide sequences within the template at both ends of or flanking the nucleotide sequence to be amplified, although primers complementary to the nucleotide sequence to be amplified also may be used. See Wang, et al., in *PCR Protocols*, pp.70-75 (Academic Press, 1990); Ochman, et al., in *PCR Protocols*, pp. 219-227; Triglia, et al., *Nuc. Acids Res.* 16:8186 (1988).

"PCR cloning" refers to the use of the PCR method to amplify a specific desired nucleotide sequence present amongst the nucleic acids from a suitable cell or tissue source, including total genomic DNA and cDNA transcribed from total cellular RNA. See Frohman, et al., *Proc. Nat. Acad. Sci. USA* 85:8998-9002 (1988); Saiki, et al., *Science* 239:487-492 (1988); Mullis, et al., *Meth. Enzymol.* 155:335-350 (1987).

"Stringent conditions" for hybridization or annealing of nucleic acid molecules are those that (1) employ low ionic strength and high temperature for washing, for example 0.015 M NaCl/0.0015 M sodium citrate/0.1% sodium dodecyl sulfate (SDS) at 50 □C, or (2) employ during hybridization a denaturing agent such as formamide, for example 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42 □C. Another example is use of 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 □g/mL), 0.1% SDS, and 10% dextran sulfate at 42 □C, with washes at 42 □C in 0.2×SSC and 0.1% SDS.

"ARX nucleic acid" is RNA or DNA which encodes ARX. "ARX DNA" is DNA which encodes ARX. ARX DNA is obtained from cDNA or genomic DNA libraries, or by in vitro synthesis. Identification of ARX DNA within a. CDNA or a genomic DNA library, or in some other mixture of various DNAs, is conveniently accomplished by the use of an oligonucleotide hybridization probe that is labeled with a detectable moiety, such as a radioisotope. See Keller, et al., *DNA Probes*, pp.149-213 (Stockton Press, 1989). To identify DNA encoding ARX, the nucleotide sequence of the hybridization probe is preferably selected so that the hybridization probe is capable of hybridizing preferentially to DNA encoding the ARX amino acid sequence set out in SEQ ID NO:2, or a variant or derivative thereof as described herein, under the hybridization conditions chosen. Another method for obtaining ARX nucleic acid is chemically synthesis, for example using one of the methods described by Engels, et al., *Agnew. Chem. Int. Ed. Engl.* 28:716-734 (1989).

If the entire nucleotide coding sequence for ARX is not obtained in a single cDNA, genomic DNA, or other DNA, as determined by DNA sequencing or restriction endonuclease analysis, then appropriate DNA fragments (e.g., restriction fragments or PCR amplification products) may be recovered from several DNAs and covalently joined to one another to construct the entire coding sequence. The preferred means of covalently joining DNA fragments is by ligation using a DNA ligase enzyme, such as T4 DNA ligase.

"Isolated" ARX nucleic acid is ARX nucleic acid which is identified and separated from, or otherwise substantially free from, contaminant nucleic acid encoding other polypeptides. The isolated ARX nucleic acid can be incorporated into a plasmid or expression vector, or can be labeled for diagnostic and probe purposes, using a label as described further.

For example, isolated ARX DNA, or a fragment thereof comprising at least about 15 nucleotides, is used as a hybridization probe to detect, diagnose, or monitor disorders or diseases that involve changes in ARX expression.

Figure 1B:
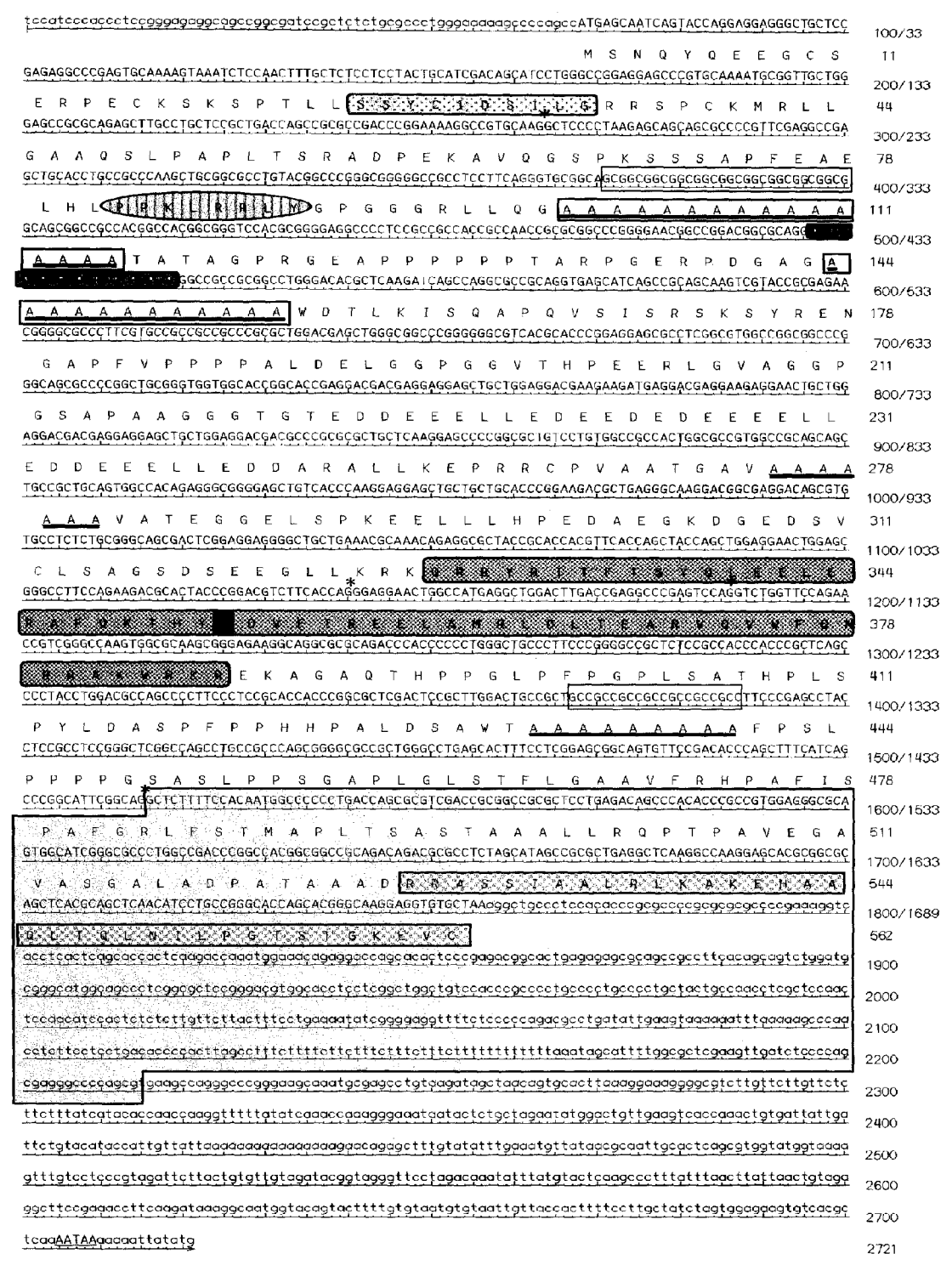
Figure 2:
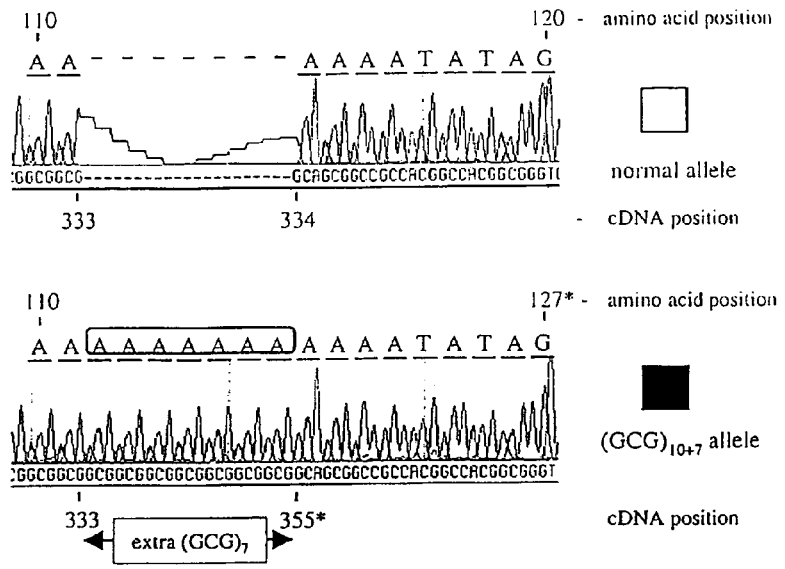
FIGS. 2a-b are DNA sequence chromatograms showing the $(GCG)_{10+7}$ and the 428-451 dup (24 bp) mutations, respectively. Protein translation (SEQ ID NOs:28, 30, 32, and 34) and amino acid position is indicated above and the cDNA sequence (SEQ ID NOs:27, 29, 31 and 33) and ORF position of ARX below the chromatograms. The extra alanine (A) residues of the ARX protein resulting from these two mutations are highlighted by rounded rectangles. The expansion of $(GCG)_7$ and duplication of 24 bb are indicated by arrows. Empty and solid squares indicate normal and affected male chromosomes. Asterisks indicate altered amino acid and cDNA positions of the ARX gene as a consequence of the two mutations.
Figure 2:
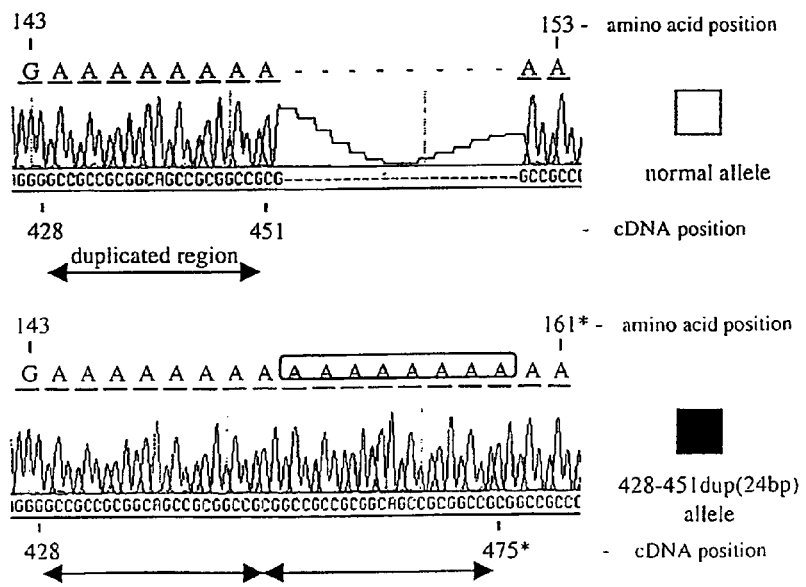

Preliminary transcriptional mapping of the minimal ISSX interval identified only ~20 genes. The human Aristaless related homeobox gene (ARX) was identified in the genomic sequence of the PAC clone 258N20 (GenBank AC002504), in the vicinity of the POLA (DNA polymerase alpha) gene (FIG. 1a). The ARX gene was screened for mutations in five families. In four of these families alterations of the ARX sequence were detected. In the family of Bruyere et al. (ref. 9), and family A of Claes et al. (ref. 11) an additional stretch of $(GCG)_7$ repeats within the normal repeat size of $(GCG)_{10}$ (exon 2) was found (FIG. 1b and 2a). In the family B of Claes et al. (ref. 11) no mutation was found. The family of Strømme et al. (ref. 10) had a duplication of 24 bp (428-451 dup (24 bp)) of exon 2 (see FIG. 1b and 2b). This 24-bp sequence is an almost perfect inverted repeat. A small Norwegian family was found to have a deletion of 1 517 bp, which removes 816 bp of intron 4 and 701 bp of exon 5 (IVS4-816_EX5701de1). This deletion results in an alternate COOH end of the ARX protein (R483fs; FIG. 1b). Both the expansion $(GCG)_{10+7}$ and the duplication mutations are predicted to cause expansions of two different polyalanine (polyA) tracts of the ARX protein. For the former mutation the normal 16 A tract (amino acid positions 100-115) is expanded to 23, and for the latter the normal 12 A tract (amino acid positions 144-155) is expanded to 20 (FIG. 2a and b). No such changes of the ARX gene were detected on more than 300 control chromosomes screened. The (GCG) repeat was found to be invariable.

Figure 3:
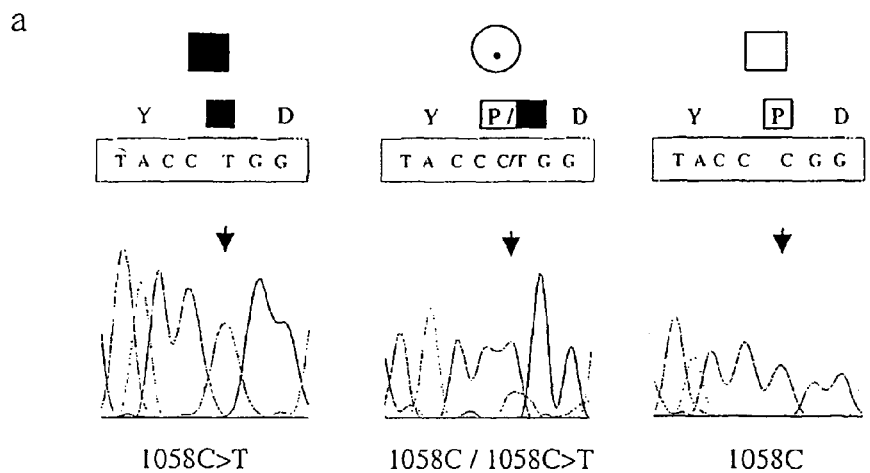
FIG. 3a-c are chromatograms, restriction analysis and sequence alignment showing the ARX mutation 1058C>T (P353L), respectively. Partial sequence chromatograms of exon 2 of ARX of one affected male (left), one carrier female (middle), and a normal male (right) are shown in FIG. 3a. The position of the mutation is indicated with an arrow. Resulting amino acid sequence is shown above the chromatograms with the resulting proline (P)-to-leucine (L) change highlighted.
Figure 3:
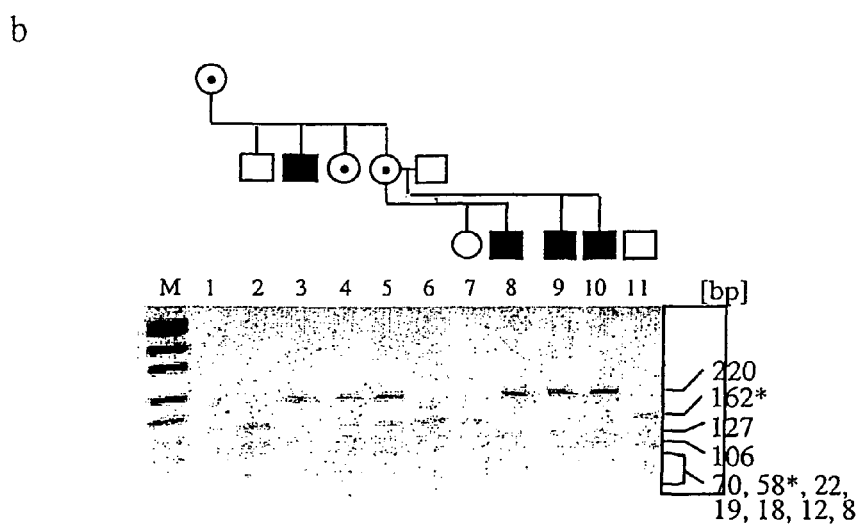
Figure 3:
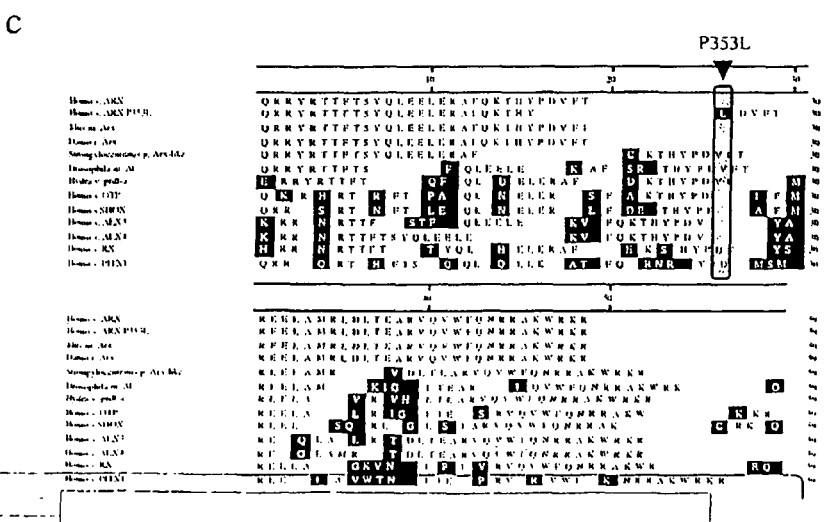

Previously, genes mutated in syndromic X-linked mental retardation (XLMR) have also been shown to carry mutations responsible for other syndromic (MRXS) as well as non-specific forms (MRX; for review see refs 1 and 12). Consequently the ARX gene was screened in six Xp22-linked XLMR families with various clinical manifestations. Two families with MRX (MRX-M and MRX-E), two families with MR and dystonic movements of the hands (Partington syndrome, PRTS MIM 309510; ref. 13 and S.F), one family with mental retardation and a history of hypsarrhythmia (MRXS-B), and one family with myoclonic epilepsy, intellectual disability and spasticity were screened. The results of this screening were as follows. One of the two MRX families (MRX-M) and both PRTS families were found to have the same duplication of the 24 bp of exon 2 as the family of Strømme et al (ref. 10). i.e. 428-451 dup (24 bp). There was no mutation found in the second MRX family (MRX-V) tested. Screening of the X-linked myoclonic epilepsy family identified a missense mutation at nucleotide position 1058, 1058C>T (FIG. 3a and b). This mutation is predicted to cause a change of proline 353 to leucine (P353L). The P353 residue is highly conserved and is one of the six invariant residues typical of the paired type of homeodomain (P26 residue; FIG.

3c). Based on the highly conserved nature of this P353 and the fact that a similar change has not been found on at least 100 control X-chromosomes tested, we predict that this represents a novel ARX gene mutation.

To test the possibility that the identical mutations, i.e. $(GCG)_{10+7}$ and 428-451 dup (24 bp), were derived from founder chromosome(s), haplotype analysis using closely linked flanking STS markers was performed. Four markers from the region were used; two distal DXS8099 and DXS8027 (~500 and 220 kb distal to ARX), and two proximal DXS8047 and DXS1202 (~300 and 600 kb proximal to ARX). The identical ARX mutations were all on different haplotypes. This supports independent, de novo origins of identical mutations in each family. We speculate that the recurrence of the 428-451 dup (24 bp) mutation may be due to the inverted repeat nature of the duplicated 24-bp sequence and its consequent instability, as indicated by our inability to clone the 428-451 dup (24 bp) mutation in *E. coli*. The apparently invariant $(GCG)_{10}$ repeat expanded by $(GCG)_7$ in two cases. Such repeats are known to form secondary structures, which solely or in addition to other cis- and trans-acting factors could contribute to repeat expansion.

ARX is a novel human homeodomain containing gene. In order to characterize it, we have used available genomic, EST and protein database resources (see Materials and Methods). The ARX gene is located about 6.7 kb from the 3' end of the POLA gene (tail-to-tail orientation; Fig 1*a*) and encompasses a genomic region of about 12.5 kb. It is composed of 5 coding exons and is transcribed into a ~2.8-kb mRNA (FIG. 1*b*). The open reading frame is 1 686-bp long and encodes a protein of 562 amino acids. Preliminary analysis of the expression of the human ARX gene by. human multiple tissue Northern blot and EST analysis indicates that it is expressed predominantly in fetal and adult brain (occipital, frontal, and temporal lobes of the cerebral cortex, amygdala, corpus callosum, caudate nucleus and hippocampus) and skeletal muscle. While in brain only a single ARX mRNA isoform was detected, skeletal muscle showed two additional, smaller ARX mRNAs, the origin of which remains to be determined.

The mouse and zebra fish ARX orthologs have been characterized by in situ hybridization to be expressed predominantly in forebrain (cerebral cortex) and floor plate. This expression pattern may suggest an important role for the ARX protein in the maintenance of specific neuronal subtypes in the cerebral cortex and axonal guidance in the floor plate.

The ARX protein belongs to a subset of Aristaless-related Paired-class homeodomain proteins. Homeobox containing genes have been shown to participate in crucial developmental decisions. While not wishing to be bound by theory, it is believed that Aristaless-related homeobox genes might regulate essential events during vertebrate embryogenesis and head development in particular. The Aristaless-related class of homeodomain proteins is characterized by either a Paired/Q50 or Paired/K50 homeodomain and a C-terminal domain called the aristaless domain (also known as OAR domain, C-peptide, or 'Paired tail'). The functionally characterized domains of the ARX protein are annotated in FIG. 1*b*. Comparison of the ARX protein to its partially characterized vertebrate orthologs reveals 94.3% and 57.2% identity with mouse and zebrafish, respectively. The octapeptide, nuclear localization sequence (NLS) and homeobox domains are identical, while the C-terminal aristaless domain is identical between human and mouse and highly similar (87%) between human/mouse and zebrafish. Conservation in the regions of the expanded polyA tracts (amino acids 100-115 and 144-155 on human ARX) between human and mouse is not 100% and the two tracts are entirely absent in zebrafish. There are two additional polyA tracts within the ARX protein (amino acids 275-281 and 431-439; FIG. 1*b*), with only the C-terminal tract being highly conserved. The function of such extended polyA tracts, common among homeobox and other transcription factor proteins, is not known, but it has been suggested that such tracts might suppress transcription.

There appears to be a positive correlation between the length of the polyA expansion and the severity of the disorder. Our results provide evidence that $(GCG)_{10+7}$ mutations, causing expansion from 16 to 23 Ala in the ISSX families, are of a more severe nature than those caused by the 428-451 dup (24 bp) mutations (from 12 to 20 Ala). Experiments with green fluorescent protein tagged polyA peptides of various lengths further support this correlation and suggest a threshold for aggregate formation of between 7 and 19 alanine residues.

The family of human homeodomain-containing genes has at least 129 members spread throughout the genome. The highly conserved 180-bp homeobox region encodes a helix-turn-helix motif known to bind specific DNA sequences. Homeodomain proteins function as crucial developmental transcription factors. Mutations of several homeobox-containing genes are known to cause human disease. The 1058C>T/P353L mutation of the myoclonic epilepsy family is the only homeodomain mutation found in this study. Although not directly involved in the homeodomain target sequence recognition, this residue is predicted to play an important role in the homeodomain structure determination by providing the proper hydrophobic environment.

The phenotypic variability of profound to mild mental retardation, infantile spasms, myoclonic epilepsy, or dystonia, associated with rather different ARX gene mutations is striking and difficult to explain. In our cohort of patients from nine families with ARX gene mutations we collected data on 51 affected individuals; 57% had seizures of various types, most commonly infantile spasms. All patients had clearly identified mental retardation with ~⅔ in the moderately to profoundly impaired range. Additional neurological abnormalities associated with ARX mutations included micro and macrocephaly, hypotonia, spasticity, and ataxia. From among the mutations found, the IVS4-816_EX5701del/R483fs mutation caused perhaps the most severe phenotype with severe developmental delay, infantile spasms, microcephaly and spasticity. The severity of the two polyA mutations, $(GCG)^{10+7}$ and 428-451 dup (24 bp) was similar although especially for the latter one, the range of clinical manifestations was broad, including ISSX, PRTS, MRX and MRXS. The phenotype of the 1058C>T/P353L mutation shared similarities with the phenotypes described above with MR, early onset of seizures (3 months to 2 years), and hypsarrhythmia in some males, but differed with myoclonic epilepsy and spasticity being prominent features.

Identification of the ARX gene represents identification of i, the first gene for idiopathic infantile spasms; ii, a new class of gene for idiopathic epilepsy, other than an ion channel; iii, one of a group of genes involved in both syndromic and non-specific XLMR; and iv, a new gene implicated in dystonia. ARX represents an X-linked gene of major significance to human cognitive function, similar to FM1, FMR2, ATRX, or MECP2 (ref.1). The ARX gene is readily amenable to screening in the same patient group with developmental delay that is now routinely tested for fragile X syndrome as described, for example, in U.S. Pat. No. 6,197,500, the contents of which are incorporated herein by reference.

A probe is designed and used for diagnosis (e.g., prenatal diagnosis or carrier detection) by standard technology utilizing means to detect hybridization of the probe under appropriate stringency conditions to the abnormal sequence. Any suitable means for detection of hybridization can be used, including radioactive or fluorescent labeling of the probe. For effective use as a probe, a fragment of the 150 kb segment may be 10 to 10,000 nucleotides in length, preferably 50 to 1000 nucleotides in length, more preferably 100 1000 nucleotides in length. The probe may be prepared by enzymatic digestion of a larger fragment of DNA or may be synthesized.

There are many different types of DNA mutations. They can be stratified based on the type of the defect as: large deletions (in tens to hundreds base pairs), small deletions (ibase pair to tens base pairs), single nucleotide changes (missense, silent and non-sense), duplications and inversions. Most of these can be found in exons, but not only. Often intronic mutations are present, some 5' and 3' UTR mutations as well as promoter mutations.

Based on the type of the mutation (and the required throughput/detection rate) a particular technique is employed. There are techniques which scan for known (previously detected) mutations like direct DNA sequencing, SSCP—single strand conformational polymorphism analysis, DGGE—denaturing gradient gel electrophoresis (ref 33), allele specific PCR, DHPLC—denaturing high-performance liquid chromatography (ref 55), MALDI TOF MS—Matrix-assisted laser desorption/ionization-time of flight mass spectrometry (ref 34), microarrays (ref 37), or Southern blot techniques.

Mutation screening strategy for research purposes (low throughput, high mutation detection rate, high cost/sample) often differs from mutation detection for diagnostic applications (high throughput, moderate mutation detection rate, low cost/sample).

Which technique is applied for diagnostic or screening purposes depends on a particular mutation. For example, the ARX duplication mutation (428-451 dup 24bp) and the GCG insertion (GCG10+7) can easily be detected using SSCP, agarose gel electrophoresis, or DHPLC. Point mutation like 1058C>T can be detected by SSCP and DHPLC, but also using array technology.

Array technology has the power to screen for any single nucleotide change in a given sequence (for example the Affymetrics type DNA chip). Therefore, it is convenient to use a microarray (Ref 37) comprising probes according to the invention for diagnosis. Typically, the microarray will comprise wild-type and mutated ARX oligonucleotides. Hybridization of patient DNA to such an array is detected and pattern generated is scored from wild-type versus mutated oligonucleotides (all possible variations) to identify the altered nucleotide.

Further, by altering the stringency of the conditions of hybridization the sequences corresponding to the locus can be isolated from normal subjects, sequenced, and corresponding sequences used in genetic therapy to correct this defect. Thus, the present invention also provides a method to treat ARX-related disorders which method comprises replacing, repairing or compensating a mutant ARX gene of the X chromosome of a subject with the corresponding DNA of a normal chromosome.

Oligonucleotides for use as hybridization probes or primers may be prepared by any suitable method, such as by purification of a naturally-occurring DNA or by in vitro synthesis. For example, oligonucleotides are readily synthesized using various techniques in organic chemistry, such as those described by Narang, et al., *Meth. Enzymol.* 68:90-98 (1979); Brown, et al., *Meth. Enzymol.* 68:109-151 (1979); Caruther, et al., *Meth. Enzymol.* 154:287-313 (1985). The general approach to selecting a suitable hybridization probe or primer is well known; see Keller, et al., *DNA Probes*, pp.11-18 (Stockton Press, 1989). Typically, the hybridization probe or primer will contain 10-25 or more nucleotides, and will include at least 5 nucleotides on either side of the sequence encoding the desired mutation so as to ensure that the oligonucleotide will hybridize preferentially to the single-stranded DNA template molecule.

The availability of cloned sequences from the ARX locus also makes possible the identification of a protein product encoded by the cloned sequences. Such proteins may be identified by operably linking the cloned sequences to a promoter in an expression vector. Many appropriate expression vectors for this purpose are widely known in the art. See, for example, Sambrook, et al., Molecular Cloning: A Laboratory Manual, 1990, Cold Spring Harbor Press, Cold Spring Harbor, N.Y. The protein product may be used for diagnostic or therapeutic purposes. Thus, for example, the presence, absence, or alteration of the protein product may correspond to the status of an affected individual. Similarly, the protein product from a normal individual may be used to treat an affected individual with an altered protein product.

Isolated ARX nucleic acid may be used to produce ARX by recombinant DNA and recombinant cell culture methods. In various embodiments of the invention, host cells are transformed or transfected with recombinant DNA molecules comprising an isolated DNA of the invention, to obtain expression of the DNA and thus the production of ARX in large quantities. DNA encoding amino acid sequence variants of ARX is prepared by a variety of methods known in the art. These methods include, but are not limited to, isolation from a natural source (in the case of naturally-occurring amino acid sequence variants of ARX or preparation by site-directed (or oligonucleotide-mediated) mutagenesis, PCR mutagenesis, and cassette mutagenesis of an earlier prepared DNA encoding a variant or a non-variant form of ARX.

Site-directed mutagenesis is a preferred method for preparing substitution, deletion, and insertion variants of ARX DNA. Briefly, in carrying out site-directed mutagenesis of ARX DNA, the DNA is altered by first hybridizing an oligonucleotide encoding the desired mutation to a single strand of such DNA. After hybridization, a DNA polymerase is used to synthesize an entire second strand, using the hybridized oligonucleotide as a primer, and using the single strand of DNA as a template. Thus, the oligonucleotide encoding the desired mutation is incorporated in the resulting double-stranded DNA.

DNA, whether cDNA or genomic DNA or a product of in vitro synthesis, may be ligated into a replicable vector for further cloning or for expression. "Vectors" are plasmids and other DNAs that are capable of replicating autonomously within a host cell, and as such, are useful for performing two functions in conjunction with compatible host cells (a vector-host system). One function is to facilitate the cloning of the nucleic acid that encodes the gene product, i.e., to produce usable quantities of the nucleic acid. The other function is to direct the expression of the gene product. One or both of these functions are performed by the vector-host system. The vectors will contain different components, depending upon the function they are to perform as well as the host cell with which they are to be used for cloning or expression.

To produce ARX or its variants, an expression vector will contain nucleic acid that encodes the desired product, as described above. In one example of recombinant host cell expression, mammalian cells are transfected with an expression vector comprising ARX DNA and the product is recovered from the culture medium in which the recombinant host cells are grown. It will be clearly understood that the expression vectors and methods disclosed herein are suitable for use over a wide range of prokaryotic and eukaryotic organisms.

Various methods of transformation and transfection are available, depending on the nature of the host cell. In the case of *E. coli* cells, the most common methods involve treating the cells with aqueous solutions of calcium chloride and other salts. In the case of mammalian cells, the most common methods are transfection mediated by either calcium phosphate or DEAE-dextran, or electroporation. See Sambrook, et al., eds., *Molecular Cloning*, pp. 1.74-1.84 and 16.30-16.55 (Cold Spring Harbor Laboratory Press, 1989). Following transformation or transfection, the desired nucleic acid may integrate into the host cell genome, or may exist as an extra-chromosomal element.

Host cells transformed or transfected with the above-described plasmids and expression vectors are cultured in conventional nutrient medium modified as is appropriate for inducing promoters or selecting for drug resistance or some other selectable marker or phenotype. The culture conditions, such as temperature, pH, and the like, suitably are those previously used for culturing the host cell used for cloning or expression, as the case may be, and will be apparent those skilled in the art.

Suitable host cells for cloning or expressing the vectors herein are prokaryotes, yeasts, and higher eukaryotes, including insect, vertebrate, and mammalian host cells.

Furthermore, monoclonal or polyclonal antibodies against the protein product may be raised by a wide variety of techniques widely known in the art. These antibodies may be labeled and used in a variety of immunoassays, or, as described above, for therapeutic use in an affected individual. See, for example, Harlow, et al., Antibodies: A Laboratory Manual, 1988, Cold Spring Harbor Press, Cold Spring Harbor, N.Y.

ARX or its variants may be used as an immunogen to generate anti-ARX antibodies. Such antibodies, which specifically bind to ARX, are useful as standards in assays for ARX, such as by labeling purified ARX for use as a standard in a radioimmunoassay, enzyme-linked immunoassay, or competitive-type receptor binding assays radioreceptor assay, as well as in affinity purification techniques. Ordinarily, the anti-ARX antibody will bind ARX with an affinity of at least about $10^6$ L/mole, and preferably at least about $10^7$ L/mole.

Polyclonal antibodies directed toward ARX generally are raised in animals by multiple subcutaneous or intraperitoneal injections of ARX and an adjuvant. It may be useful to conjugate ARX or a peptide fragment thereof to a carrier protein that is immunogenic in the species to be immunized, such as keyhole limpet hemocyanin, serum albumin, bovine thyroglobulin, or soybean trypsin inhibitor.

Monoclonal antibodies directed toward ARX are produced using any method which provides for the production of antibody molecules by continuous cell lines in culture. The modifier "monoclonal" indicates the character of the antibody as being obtained from a substantially homogeneous population of antibodies, and is not to be construed as requiring production of the antibody by any particular method. Examples of suitable methods for preparing monoclonal antibodies include the original hybridoma method of Kohler, et al., *Nature* 256:495-497 (1975), and the human B-cell hybridoma method, Kozbor, *J. Immunol.* 133:3001 (1984); Brodeur, et al., *Monoclonal Antibody Production Techniques and Applications*, pp. 51-63 (Marcel Dekker, Inc., New York, 1987).

The monoclonal antibodies of the invention specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly, et al., U.S. Pat. No. 4,816,567; Morrison, et al., *Proc. Natl. Acad. Sci.* 81:6851-6855 (1984)).

The chimeric antibody may be a "humanized" antibody. Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain.

Humanization can be performed following methods known in the art (Jones, et al., *Nature* 321:522-525 (1986); Riechmann, et al., *Nature,* 332:323-327 (1988); Verhoeyen, et al., *Science* 239:1534-1536 (1988)), by substituting rodent complementarity-determining regions (CDRs) for the corresponding regions of a human antibody. Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, for example, Jakobovits, et al., *Proc. Natl. Acad. Sci.* 90: 2551-2555 (1993); Jakobovits, et al., *Nature* 362:255-258 (1993); Bruggermann, et al., Year in Immuno. 7:33 (1993). Human antibodies can also be produced in phage-display libraries (Hoogenboom, et al., *J. Mol. Biol.* 227:381 (1991); Marks, et al., *J. Mol. Biol.* 222:581 (1991).

For diagnostic applications, anti-ARX antibodies typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; radioactive isotopic labels, such as, e.g., $^{125}I$, $^{32}p$, $^{14}C$, or $^3H$, or an enzyme, such as alkaline phosphatase, beta-galactosidase or horseradish peroxidase.

Any method known in the art for separately conjugating the antibody to the detectable moiety may be employed, including those methods described by David, et al., *Biochemistry* 13:1014-1021 (1974); Pain, et al., *J. Immunol. Meth.* 40:219-231 (1981); and Bayer, et al., Meth. Enz. 184:138-163 (1990).

The anti-ARX antibodies may be employed in any known assay method, such as competitive binding assays, direct and indirect sandwich assays, and immunoprecipitation assays. Zola, *Monoclonal Antibodies: A Manual of Techniques*, pp. 147-158 (CRC Press, Inc., 1987). Neutralizing anti-ARX antibodies are useful as antagonists of ARX.

Materials and Methods

ISSX Families

Four large, mapped X-linked families were analyzed. These included two families of Claes et al. (ref. 11), and one family each from Strømme et al. (ref. 10) and Bruyere et al. (ref. 9). Another small family with infantile spasms from Norway was available for analysis. The patient is a 2-year-old boy whose development from birth was severely delayed with lack of eye contact, poor head control, decreased limb movements, and increased muscle tone. Seizures were noted at 4½ weeks progressing to culminant infantile spasms with hypsarrhythmia, refractory to vigabatrin, ACTH, and multiple antiepileptic drugs. During the first year microcephaly with unilateral flattening of the skull, right microphthalmia and delayed myelination on MRI were observed. One maternal uncle died at 20 months of age with infantile spasms and severe developmental delay.

Bioinformatic Analyses

The map of the candidate ISSX/WS DXS1226/AHC .about.7 cM region was initially accessed at the Baylor College of Medicine URL site ( kiwi.imgen.bcm.tmc.edu:8088/cgi-bin/seq/home/) and further refined using Ensembl at: ensembl.org/. Genomic sequence of the PAC RPCI1-258N20 was masked for repeat sequences using Repeat Masker at ftp.genome.washington.edu/cgi-bin/RepeatMasker. Masked sequence was searched against nr and EST divisions of the GenBank database using Blast (ncbi.nlm.nih.gov/cgi-bin/BLAST/). DNA and protein sequences of the known genes as well as ESTs (GenBank; ncbi.nlm.nih.gov/), and Unigene clusters (ncbi.nlm.nih.gov/UniGene/index.html) were downloaded and further manipulated using the Lasergene software package (DNA Star).

Mutation Search

Primer pairs were designed from the genomic sequence flanking each of the five exons of the ARX gene. For exon 2 two overlapping PCR products P1 and P2 were designed. The primers, $T_m$ for the annealing step of the PCR and sizes of the genomic. PCR products were as follows: exon 1, 520-bp product ($T_m=63°$ C.), 1F (5'-GCTCACTACACTTGTTAC-CGC-3'-SEQ ID NO:12) and 1R (5'-AATTGACAATTC-CAGGCCACTG-3'-SEQ ID NO:13); exon 2P1, 584-bp product ($T_m=62°$ C.), 2P1F (5'-ACGCCTGGGCCTAG-GCACTG-3'-SEQ ID NO:14) and 2P1R (5'-CTCGGTGC-CGGTGCCACCAC-3'-SEQ ID NO:15); exon 2P2, 602-bp product ($T_m=62°$ C.) , 2P2F (5'-GCAAGTCGTACCGC-GAGAACG-3' SEQ ID NO:16) and 2P2R (5'-TGCGCTCTCTGCCGCTGCGA-3'-SEQ ID NO:17); exon 3, 231-bp product ($T_m=60°$ C.) , 3F (5'-GAAATAGCT-GAGAGGGCATTGC-3'-SEQ ID NO:18) and 3R (5'-TCTCTTGGTTTTGTGAAGGGGAT-3' SEQ ID NO:19); exon 4, 551-bp product ($T_m=60°$ C.) , 4F (5'-GACGCGTC-CGAAAACAACCTGAG-SEQ ID NO:20) and 4R (5'-CCCCAGCCTCTGTGTGTATG-3'-SEQ ID NO:21); and exon 5, 347-bp product ($T_m=60°$ C.) , 5F (5'-ACAGCTC-CCGAGGCCATGAC-3'-SEQ ID NO:22) and 5R (5'-GAGTGGTGCTGAGTGAGGTGA-3'-SEQ ID NO:23). We found the PCR amplification of the ARX exons of poor reproducibility due most probably to an unusually high GC content. Ultimately we have optimized the conditions using Failsafe buffer J (EPICENTRE Technologies) and Expand Long Template Enzyme Mix (Roche). Usually up to 35 PCR cycles of denaturation at 94° C. for 30 sec, annealing at 60-63° C. for 30 sec and extension at 68° C. for 2 min were carried out on 50-100 ng of genomic DNA with 0.5 µM PCR primers, 200 mM dNTPs, 2.5 U of Expand Long Template Enzyme Mix (Roche), and 1x Failsafe buffer J (EPICENTRE Technologies).

As controls, 300 chromosomes were tested by denaturing polyacrylamide electrophoresis (5% gel) for the presence of either the $(GCG)_{10+7}$ or 428-451 dup (24 bp) exon 2 ARX mutations. There were no such alleles detected in this sample set. It is also notable that the homogeneous repeat $(GCG)_{10}$ (position 314-333) is invariable as all chromosomes tested showed only the $(GCG)_{10}$ allele. For the 1058C>T transition, 100 chromosomes were tested by PCR followed by restriction digest with MspI. The following restriction fragments are generated (in 5'-3' order) from a normal allele: 70, 18, 22, 8, 12, 19, 127, 106, 162 and 58-bp, respectively. The 1058C>T mutation abolishes the most 3' end restriction site generating a larger 220-bp product instead of two 162 and 58-bp products (see FIG. 2b). Among the 100 control chromosomes tested, no 1058C>T alleles were found.

Dye terminator (Big Dye Terminator) sequencing was performed according to the instructions of the supplier of the kit (Perkin Elmer). Exon PCR products were purified using UltraCleanTM PCR Clean-up DNA purification kit (MoBio Laboratories, Inc.). All exons were sequenced in both forward and reverse directions.

Hybridisation Probe

The ARX probe for Southern blot hybridization of the deletion patient (see above) and Northern multiple tissue blots (Clontech) was generated from the 3' untranslated region using the following primers: F, 5'-GCGAGGGC-CCCAGCGTGAAG-3'-SEQ ID NO:24 and R, 5'-GCCTG-TATGGAGCATTCACAC-3'-SEQ ID NO:25 (557-bp product).

GenBank Accession Numbers

PAC genomic sequence data, AC002504 and AC004655; human ARX MRNA Ensembl ID:ENSG00000004848; mouse Arx mRNA, AB006103; zebrafish Arx mRNA, AB006104, and fly aristaless protein, AAF51505.

REFERENCES

The contents of the following documents are incorporated herein by reference:

1. Chelly, J. & Mandel, J. L. Monogenic causes of X-linked mental retardation. Nat. Rev. Genet. 2, 669-680 (2001).
2. Berkovic, S. F. & Scheffer, I. E. Genetics of the Epilepsies. Epilepsia 42(Suppl. 5), 16-23 (2001).
3. Sugawara, T. et. al. A missense mutation of the Na+ channel alpha II subunit gene Na(v)1.2 in a patient with febrile and agebrile seizures causes channel dysfunction. Proc. Natl. Acad. Sci. U S A 98, 6384-6389 (2001).
4. Brais, B. et al. Short GCG expansions in the PABP2 gene cause oculopharyngeal muscular dystrophy. Nat. Genet. 18, 164-167 (1998).
5. Gusella, J. F. & MacDonald, M. E. Molecular genetics: unmasking polyglutamine triggers in neurodegenerative disease. Nat. Rev. Neurosci. 1, 109-115 (2000).
6. Wong, M. & Trevathan, E. Infantile spasms. Pediatr. Neurol. 24, 89-98 (2001).
7. Vigevano, F. et al. The idiopathic form of West syndrome. Epilepsia 34, 743-746 (1993).
8., Feinberg, A. P. & Leahy, W. R. Infantile spasms: case report of sex-linked inheritance. Dev. Med. Child. Neurol. 19, 524-526. (1977).
9. Bruyere, H., Lewis, S., Wood, S., MacLeod, P. J. & Langlois, S. Confirmation of linkage in X-linked infantile spasms (West syndrome) and refinement of the disease locus to Xp21.3-Xp22.1. Clin. Genet. 55, 173-181 (1999).
10. Strømme, P. et al. X linked mental retardation and infantile spasms in a family: new clinical data and linkage to Xp11.4-Xp22.11. J. Med. Genet. 36, 374-378 (1999).
11. Claes, S. et al. The X-linked infantile spasms syndrome (MIM 308350) maps to Xp11.4-Xpter in two pedigrees. Ann. Neurol. 42, 360-364 (1997).
12. Stevenson, R. E. Splitting and lumping in the nosology of XLMR. Am. J. Med. Genet. 97, 174-182 (2000).
13. Partington, M. W. et al. X-linked mental retardation with dystonic movements of the hands. Am. J. Med. Genet. 30, 251-262 (1988).

14. Galliot, B., de Vargas, C. & Miller, D. Evolution of homeobox genes: Q50 Paired-like genes founded the Paired class. *Dev. Genes. Evol.* 209, 186-197 (1999).
15. Richards, R. I. Dynamic mutations: a decade of unstable expanded repeats in human genetic disease. *Hum. Mol. Genet.* 10, 2187-2194 (2001).
16. Miura, H., Yanazawa, M., Kato, K. & Kitamura, K. Expression of a novel aristaless related homeobox gene 'Arx' in the vertebrate telencephalon, diencephalon and floor plate. *Mech. Dev.* 65, 99-109 (1997).
17. Ohira, R. et al. Aristaless related homeobox (ARX) gene is expressed in a subset of neuronal precursor cells and post-mitotic neurons in human fetal and adult brain. *Am. J. Hum. Genet.* 67, Supplement 2, 169 (2000).
18. Meijlink, F., Beverdam, A., Brouwer, A., Oosterveen, T. C. & Berge, D. T. Vertebrate aristaless-related genes. *Int. J. Dev. Biol.* 43, 651-663 (1999).
19. Galliot, B. & Miller, D. Origin of anterior patterning. How old is our head? *Trends Genet.* 16, 1-5. (2000).
20. Han, K. & Manley, J. Functional domains of the Drosophila Engrailed protein. *EMBO J.* 12, 2723-2733 (1993).
21. Muragaki, Y., Mundlos, S., Upton, J. & Olsen, B. R. Altered growth and branching patterns in synpolydactyly caused by mutations in HOXD13. *Science* 272, 548-551 (1996).
22. Mundlos, S. et al. Mutations involving the transcription factor CBFA1 cause cleidocranial dysplasia. *Cell* 89, 773-779 (1997).
23. Brown, S. A. et al. Holoprosencephaly due to mutations in ZIC2, a homologue of Drosophila odd-paired. *Nat. Genet.* 20, 180-183 (-1998).
24. Goodman, F. R. et al. Novel HOXA13 mutations and the phenotypic spectrum of hand-foot-genital syndrome. *Am. J. Hum. Genet.* 67, 197-202 (2000).
25. Crisponi, L. et al. The putative forkhead transcription factor FOXL2 is mutated in blepharophimosis/ptosis/epicanthus inversus syndrome. *Nat. Genet.* 27, 159-166 (2001).
26. Brown, L. Y. et al. Holoprosencephaly due to mutations in ZIC2: alanine tract expansion mutations may be caused by parental somatic recombination. *Hum. Mol. Genet.* 10, 791-796 (2001).
27. Calado, A. et al. Nuclear inclusions in oculopharyngeal muscular dystrophy consist of poly(A) binding protein 2 aggregates which sequester poly(A) RNA. *Hum. Mol. Genet.* 9, 2321-2328 (2000).
28. Hill, M. E. et al. Oculopharyngeal muscular dystrophy: phenotypic and genotypic studies in a UK population. *Brain* 124, 522-526 (2001).
29. Rankin, J., Wyttenbach, A. & Rubinsztein, D. C. Intracellular green fluorescent protein-polyalanine aggregates are associated with cell death. *Biochem. J.* 348 Pt 1, 15-19 (2000).
30. Gaspar, C. et al. CAG tract of MJD-1 may be prone to frameshifts causing polyalanine accumulation. *Hum. Mol. Genet.* 9, 1957-1966 (2000).
31. Banerjee-Basu, S. & Baxevanis, A. D. Molecular evolution of the homeodomain family of transcription factors. *Nucleic Acids Res.* 29, 3258-3269 (2001).
32. Wilson, D. S., Sheng, G., Jun, S. & Desplan, C. Conservation and diversification in homeodomain-DNA interactions: a comparative genetic analysis. *Proc. Natl. Acad. Sci. U S A* 93, 6886-6891 (1996).
33. Fodde R, Losekoot M.Mutation detection by denaturing gradient gel electrophoresis (DGGE). Hum Mutat. 1994;3(2):83-94. Review.
34. Leushner J. MALDI TOF mass spectrometry: an emerging platform for genomics and diagnostics. Expert Rev Mol Diagn 2001 May;1(1):11-8. Review.
35. Kristensen V N, Kelefiotis D, Kristensen T, Borresen-Dale A L. High-throughput methods for detection of genetic variation. Biotechniques. 2001 February; 30(2): 318-22. Review.
36. Nataraj A J, Olivos-Glander I, Kusukawa N, Highsmith W E Jr. Single-strand conformation polymorphism and heteroduplex analysis for gel-based mutation detection. Electrophoresis. 1999 June; 20(6):1177-85. Review.
37. McKenzie SE, Mansfield E, Rappaport E, Surrey S, Fortina P. Parallel molecular genetic analysis. Eur J Hum Genet. 1998 Sep-Oct;6(5):417-29. Review.

The invention claimed is:

1. A method of detecting the presence of a mutation in the human ARX gene comprising: isolating a nucleotide sequence comprising at least an exon of the human ARX gene from a test sample; performing an assay to compare said nucleotide sequence with the nucleotide sequence of a wild-type human ARX gene, and identifying a difference between the nucleotide sequences that is an insertion of trinucleotide repeats coding for additional alanine residues within a polyalanine tract, wherein identification of said difference between the nucleotide sequences indicates the detection of the presence of a mutation in the human ARX gene.

2. The method of claim 1, wherein the wild-type ARX gene comprises SEQ ID NO:1.

3. The method of claim 1, wherein the test sample comprises SEQ ID NO:4.

4. A method for detecting the presence of X-linked infantile spasms in a human subject comprising: isolating a nucleotide sequence comprising at least an exon of the human ARX gene from a sample obtained from the subject; performing an assay to compare said nucleotide sequence with a nucleotide sequence that encodes wild-type ARX; and identifying a difference between the nucleotide sequences that is an insertion of trinucleotide repeats coding for additional alanine residues within a polyalanine tract, wherein identification of said difference between the nucleotide sequences is indicative of the detection of the presence of X-linked infantile spasms.

5. The method of claim 4, wherein the assay is selected from the group consisting of: SSCP, PCR, DGGE, DHPLC, microarray and Southern blot-based tests.

6. The method of claim 5, wherein a sequence comparison is made by a hybridization assay.

7. A method for predicting the likelihood that a human individual will have X-linked infantile spasms, comprising isolating a nucleotide sequence comprising at least an exon of the human ARX gene from a nucleic acid sample obtained from the individual, performing an assay to compare said nucleotide sequence with a nucleotide sequence that encodes wild-type ARX; and identifying a difference between the nucleotide sequences that is an insertion of trinucleotide repeats coding for additional alanine residues within a polyalanine tract of the ARX gene, wherein said difference, is indicative of the likelihood that the individual from whom the sample was obtained will have X-linked infantile spasms.

8. The method of claim 7, wherein the nucleic acid sample comprises an mRNA sample.

9. The method of claim 8, wherein the nucleotide sequence is analyzed using specific hybridization probes.

10. The method of claim 7, wherein the nucleotide sequence is analyzed using an assay selected from the group consisting of: SSCP, PCR, DGGE, DHPLC, microarray and Southern blot-based tests.

11. The method of claim 1, wherein the mutation is an insertion of $(GCG)_7$ trinucleotide repeats within the first polyalanine tract.

* * * * *